(12) United States Patent
Coakley et al.

(10) Patent No.: US 7,684,843 B2
(45) Date of Patent: *Mar. 23, 2010

(54) MEDICAL SENSOR AND TECHNIQUE FOR USING THE SAME

(75) Inventors: Joseph Coakley, Dublin, CA (US); George L. Matlock, Pleasanton, CA (US); William Raridan, Pleasanton, CA (US); Darius Eghbal, Oakland, CA (US)

(73) Assignee: Nellcor Puritan Bennett LLC, Boulder, CO (US)

(*) Notice: Subject to any disclaimer, the term of this patent is extended or adjusted under 35 U.S.C. 154(b) by 559 days.

This patent is subject to a terminal disclaimer.

(21) Appl. No.: 11/494,838

(22) Filed: Jul. 28, 2006

(65) Prior Publication Data

US 2007/0032711 A1 Feb. 8, 2007

Related U.S. Application Data

(63) Continuation of application No. 11/199,524, filed on Aug. 8, 2005.

(51) Int. Cl.
*A61B 5/145* (2006.01)

(52) U.S. Cl. .................................................. 600/344
(58) Field of Classification Search ................. 600/310, 600/322, 323, 344; 427/2.1, 2.11, 2.12
See application file for complete search history.

(56) References Cited

U.S. PATENT DOCUMENTS

| | | |
|---|---|---|
| 3,403,555 A | 10/1968 | Versaci et al. |
| 3,536,545 A | 10/1970 | Traynor et al. |
| D222,454 S | 10/1971 | Beeber |
| 3,721,813 A | 3/1973 | Condon et al. |
| D250,275 S | 11/1978 | Bond |

(Continued)

FOREIGN PATENT DOCUMENTS

CN 11080192 11/2007

(Continued)

OTHER PUBLICATIONS

Crespi, F., et al.; "Near infrared oxymeter prototype for non-invasive analysis of rat brain oxygenation," *Optical Sensing, Proceedings of SPIE*, vol. 5459, pp. 38-45 (2004).

(Continued)

*Primary Examiner*—Eric F Winakur
*Assistant Examiner*—Etsub D Berhanu
(74) *Attorney, Agent, or Firm*—Fletcher Yoder

(57) ABSTRACT

A sensor assembly is provided that includes a frame having two or more structural supports. A coating is provided over the frame. The coating has at least one deformable region disposed between the two or more structural supports. As least one optical component is disposed within the at least one deformable region such that the at least one optical component can move relative to the two or more structural supports. A biasing component is attached to an end of the frame such that at least two different portions of the coated frame are biased closed in the absence of a sufficient opening force. The sensor may be placed on a patient's finger, toe, ear, and so forth to obtain pulse oximetry or other physiological measurements. A skeletal frame and a method for manufacturing a skeletal framework are also provided.

22 Claims, 6 Drawing Sheets

U.S. PATENT DOCUMENTS

| | | |
|---|---|---|
| D251,387 S | 3/1979 | Ramsay et al. |
| D262,488 S | 12/1981 | Rossman et al. |
| 4,334,544 A | 6/1982 | Hill et al. |
| 4,350,165 A | 9/1982 | Striese |
| 4,353,372 A | 10/1982 | Ayer |
| 4,380,240 A | 4/1983 | Jöbsis et al. |
| 4,406,289 A | 9/1983 | Wesseling et al. |
| 4,510,551 A | 4/1985 | Brainard, II |
| 4,586,513 A | 5/1986 | Hamaguri |
| 4,603,700 A | 8/1986 | Nichols et al. |
| 4,621,643 A | 11/1986 | New, Jr. et al. |
| 4,653,498 A | 3/1987 | New, Jr. et al. |
| 4,677,528 A | 6/1987 | Miniet |
| 4,685,464 A | 8/1987 | Goldberger et al. |
| 4,694,833 A | 9/1987 | Hamaguri |
| 4,697,593 A | 10/1987 | Evans et al. |
| 4,700,708 A | 10/1987 | New, Jr. et al. |
| 4,714,080 A | 12/1987 | Edgar, Jr. et al. |
| 4,714,341 A | 12/1987 | Hamaguri et al. |
| 4,722,120 A | 2/1988 | Lu |
| 4,726,382 A | 2/1988 | Boehmer et al. |
| 4,759,369 A | 7/1988 | Taylor |
| 4,770,179 A | 9/1988 | New, Jr. et al. |
| 4,773,422 A | 9/1988 | Isaacson et al. |
| 4,776,339 A | 10/1988 | Schreiber |
| 4,781,195 A | 11/1988 | Martin |
| 4,783,815 A | 11/1988 | Büttner |
| 4,796,636 A | 1/1989 | Branstetter et al. |
| 4,800,495 A | 1/1989 | Smith |
| 4,800,885 A | 1/1989 | Johnson |
| 4,802,486 A | 2/1989 | Goodman et al. |
| 4,805,623 A | 2/1989 | Jöbsis |
| 4,807,630 A | 2/1989 | Malinouskas |
| 4,807,631 A | 2/1989 | Hersh et al. |
| 4,819,646 A | 4/1989 | Cheung et al. |
| 4,819,752 A | 4/1989 | Zelin |
| 4,824,242 A | 4/1989 | Frick et al. |
| 4,825,872 A | 5/1989 | Tan et al. |
| 4,825,879 A | 5/1989 | Tan et al. |
| 4,830,014 A | 5/1989 | Goodman et al. |
| 4,832,484 A | 5/1989 | Aoyagi et al. |
| 4,846,183 A | 7/1989 | Martin |
| 4,848,901 A | 7/1989 | Hood, Jr. |
| 4,854,699 A | 8/1989 | Edgar, Jr. |
| 4,859,056 A | 8/1989 | Prosser et al. |
| 4,859,057 A | 8/1989 | Taylor et al. |
| 4,863,265 A | 9/1989 | Flower et al. |
| 4,865,038 A | 9/1989 | Rich et al. |
| 4,867,557 A | 9/1989 | Takatani et al. |
| 4,869,253 A | 9/1989 | Craig, Jr. et al. |
| 4,869,254 A | 9/1989 | Stone et al. |
| 4,880,304 A | 11/1989 | Jaeb et al. |
| 4,883,055 A | 11/1989 | Merrick |
| 4,883,353 A | 11/1989 | Hansmann et al. |
| 4,890,619 A | 1/1990 | Hatschek |
| 4,892,101 A | 1/1990 | Cheung et al. |
| 4,901,238 A | 2/1990 | Suzuki et al. |
| 4,908,762 A | 3/1990 | Suzuki et al. |
| 4,911,167 A | 3/1990 | Corenman et al. |
| 4,913,150 A | 4/1990 | Cheung et al. |
| 4,926,867 A | 5/1990 | Kanda et al. |
| 4,927,264 A | 5/1990 | Shiga et al. |
| 4,928,692 A | 5/1990 | Goodman et al. |
| 4,934,372 A | 6/1990 | Corenman et al. |
| 4,938,218 A | 7/1990 | Goodman et al. |
| 4,942,877 A | 7/1990 | Sakai et al. |
| 4,948,248 A | 8/1990 | Lehman |
| 4,955,379 A | 9/1990 | Hall |
| 4,960,126 A | 10/1990 | Conlon et al. |
| 4,964,408 A | 10/1990 | Hink et al. |
| 4,971,062 A | 11/1990 | Hasebe et al. |
| 4,974,591 A | 12/1990 | Awazu et al. |
| 5,007,423 A | 4/1991 | Branstetter et al. |
| 5,025,791 A | 6/1991 | Niwa |
| RE33,643 E | 7/1991 | Isaacson et al. |
| 5,028,787 A | 7/1991 | Rosenthal et al. |
| 5,035,243 A | 7/1991 | Muz |
| 5,040,539 A | 8/1991 | Schmitt et al. |
| 5,041,187 A | 8/1991 | Hink et al. |
| 5,054,488 A | 10/1991 | Muz |
| 5,055,671 A | 10/1991 | Jones |
| 5,058,588 A | 10/1991 | Kaestle |
| 5,065,749 A | 11/1991 | Hasebe et al. |
| 5,066,859 A | 11/1991 | Karkar et al. |
| 5,069,213 A | 12/1991 | Polczynski |
| 5,078,136 A | 1/1992 | Stone et al. |
| 5,086,229 A | 2/1992 | Rosenthal et al. |
| 5,088,493 A | 2/1992 | Giannini et al. |
| 5,090,410 A | 2/1992 | Saper et al. |
| 5,094,239 A | 3/1992 | Jaeb et al. |
| 5,094,240 A | 3/1992 | Muz |
| 5,099,841 A | 3/1992 | Heinonen et al. |
| 5,099,842 A | 3/1992 | Mannheimer et al. |
| H1039 H | 4/1992 | Tripp et al. |
| 5,104,623 A | 4/1992 | Miller |
| 5,109,849 A | 5/1992 | Goodman et al. |
| 5,111,817 A | 5/1992 | Clark et al. |
| 5,113,861 A | 5/1992 | Rother |
| D326,715 S | 6/1992 | Schmidt |
| 5,125,403 A | 6/1992 | Culp |
| 5,127,406 A | 7/1992 | Yamaguchi |
| 5,131,391 A | 7/1992 | Sakai et al. |
| 5,140,989 A | 8/1992 | Lewis et al. |
| 5,152,296 A | 10/1992 | Simons |
| 5,154,175 A | 10/1992 | Gunther |
| 5,158,082 A | 10/1992 | Jones |
| 5,170,786 A | 12/1992 | Thomas et al. |
| 5,188,108 A | 2/1993 | Secker et al. |
| 5,190,038 A | 3/1993 | Polson et al. |
| 5,193,542 A | 3/1993 | Missanelli et al. |
| 5,193,543 A | 3/1993 | Yelderman |
| 5,203,329 A | 4/1993 | Takatani et al. |
| 5,209,230 A | 5/1993 | Swedlow et al. |
| 5,213,099 A | 5/1993 | Tripp et al. |
| 5,216,598 A | 6/1993 | Branstetter et al. |
| 5,217,012 A | 6/1993 | Young et al. |
| 5,217,013 A | 6/1993 | Lewis |
| 5,218,207 A | 6/1993 | Rosenthal |
| 5,218,962 A | 6/1993 | Mannheimer et al. |
| 5,224,478 A | 7/1993 | Sakai et al. |
| 5,226,417 A | 7/1993 | Swedlow et al. |
| 5,228,440 A | 7/1993 | Chung et al. |
| 5,237,994 A | 8/1993 | Goldberger |
| 5,239,185 A | 8/1993 | Ito et al. |
| 5,246,003 A | 9/1993 | DeLonzor |
| 5,247,931 A | 9/1993 | Norwood |
| 5,247,932 A | 9/1993 | Chung et al. |
| 5,249,576 A | 10/1993 | Goldberger et al. |
| 5,253,645 A | 10/1993 | Freidman et al. |
| 5,253,646 A | 10/1993 | Delpy et al. |
| 5,259,381 A | 11/1993 | Cheung et al. |
| 5,259,761 A | 11/1993 | Schnettler et al. |
| 5,263,244 A | 11/1993 | Centa et al. |
| 5,267,562 A | 12/1993 | Ukawa et al. |
| 5,267,563 A | 12/1993 | Swedlow et al. |
| 5,267,566 A | 12/1993 | Choucair et al. |
| 5,273,036 A | 12/1993 | Kronberg et al. |
| 5,275,159 A | 1/1994 | Griebel |
| 5,278,627 A | 1/1994 | Aoyagi et al. |
| 5,279,295 A | 1/1994 | Martens et al. |
| 5,285,783 A | 2/1994 | Secker |
| 5,285,784 A | 2/1994 | Seeker |
| 5,287,853 A | 2/1994 | Vester et al. |
| 5,291,884 A | 3/1994 | Heinemann et al. |

| Patent | Date | Inventor |
|---|---|---|
| 5,297,548 A | 3/1994 | Pologe |
| 5,299,120 A | 3/1994 | Kaestle |
| 5,299,570 A | 4/1994 | Hatschek |
| 5,309,908 A | 5/1994 | Freidman et al. |
| 5,311,865 A | 5/1994 | Mayeux |
| 5,313,940 A | 5/1994 | Fuse et al. |
| 5,323,776 A | 6/1994 | Blakely et al. |
| 5,329,922 A | 7/1994 | Atlee, III |
| 5,337,744 A | 8/1994 | Branigan |
| 5,339,810 A | 8/1994 | Ivers et al. |
| 5,343,818 A | 9/1994 | McCarthy et al. |
| 5,343,869 A | 9/1994 | Pross et al. |
| 5,348,003 A | 9/1994 | Caro |
| 5,348,004 A | 9/1994 | Hollub et al. |
| 5,349,519 A | 9/1994 | Kaestle |
| 5,349,952 A | 9/1994 | McCarthy et al. |
| 5,349,953 A | 9/1994 | McCarthy et al. |
| 5,351,685 A | 10/1994 | Potratz |
| 5,353,799 A | 10/1994 | Chance |
| 5,355,880 A | 10/1994 | Thomas et al. |
| 5,355,882 A | 10/1994 | Ukawa et al. |
| 5,361,758 A | 11/1994 | Hall et al. |
| 5,365,066 A | 11/1994 | Krueger, Jr. et al. |
| 5,368,025 A | 11/1994 | Young et al. |
| 5,368,026 A | 11/1994 | Swedlow et al. |
| 5,368,224 A | 11/1994 | Richardson et al. |
| 5,372,136 A | 12/1994 | Steuer et al. |
| 5,377,675 A | 1/1995 | Ruskewicz et al. |
| 5,385,143 A | 1/1995 | Aoyagi |
| 5,387,122 A | 2/1995 | Goldberger et al. |
| 5,390,670 A | 2/1995 | Centa et al. |
| 5,392,777 A | 2/1995 | Swedlow et al. |
| 5,398,680 A | 3/1995 | Polson et al. |
| 5,402,777 A | 4/1995 | Warring et al. |
| 5,402,779 A | 4/1995 | Chen et al. |
| 5,411,023 A | 5/1995 | Morris, Sr. et al. |
| 5,411,024 A | 5/1995 | Thomas et al. |
| 5,413,099 A | 5/1995 | Schmidt et al. |
| 5,413,100 A | 5/1995 | Barthelemy et al. |
| 5,413,101 A | 5/1995 | Sugiura |
| 5,413,102 A | 5/1995 | Schmidt et al. |
| 5,417,207 A | 5/1995 | Young et al. |
| 5,421,329 A | 6/1995 | Casciani et al. |
| 5,425,360 A | 6/1995 | Nelson |
| 5,425,362 A | 6/1995 | Siker et al. |
| 5,427,093 A | 6/1995 | Ogawa et al. |
| 5,429,128 A | 7/1995 | Cadell et al. |
| 5,429,129 A | 7/1995 | Lovejoy et al. |
| 5,431,159 A | 7/1995 | Baker et al. |
| 5,431,170 A | 7/1995 | Mathews |
| 5,437,275 A | 8/1995 | Amundsen et al. |
| 5,438,986 A | 8/1995 | Disch et al. |
| 5,448,991 A | 9/1995 | Polson et al. |
| 5,452,717 A | 9/1995 | Branigan et al. |
| 5,465,714 A | 11/1995 | Scheuing |
| 5,469,845 A | 11/1995 | DeLonzor et al. |
| RE35,122 E | 12/1995 | Corenman et al. |
| 5,482,034 A | 1/1996 | Lewis et al. |
| 5,482,036 A | 1/1996 | Diab et al. |
| 5,485,847 A | 1/1996 | Baker, Jr. |
| 5,490,505 A | 2/1996 | Diab et al. |
| 5,490,523 A | 2/1996 | Isaacson et al. |
| 5,491,299 A | 2/1996 | Naylor et al. |
| 5,494,032 A | 2/1996 | Robinson et al. |
| 5,494,043 A | 2/1996 | O'Sullivan et al. |
| 5,497,771 A | 3/1996 | Rosenheimer |
| 5,499,627 A | 3/1996 | Steuer et al. |
| 5,503,148 A | 4/1996 | Pologe et al. |
| 5,505,199 A | 4/1996 | Kim |
| 5,507,286 A | 4/1996 | Solenberger |
| 5,511,546 A | 4/1996 | Hon |
| 5,517,988 A | 5/1996 | Gerhard |
| 5,520,177 A | 5/1996 | Ogawa et al. |
| 5,521,851 A | 5/1996 | Wei et al. |
| 5,522,388 A | 6/1996 | Ishikawa et al. |
| 5,524,617 A | 6/1996 | Mannheimer |
| 5,529,064 A | 6/1996 | Rall et al. |
| 5,533,507 A | 7/1996 | Potratz et al. |
| 5,551,423 A | 9/1996 | Sugiura |
| 5,551,424 A | 9/1996 | Morrison et al. |
| 5,553,614 A | 9/1996 | Chance |
| 5,553,615 A | 9/1996 | Carim et al. |
| 5,555,882 A | 9/1996 | Richardson et al. |
| 5,558,096 A | 9/1996 | Palatnik |
| 5,560,355 A | 10/1996 | Merchant et al. |
| 5,564,417 A | 10/1996 | Chance |
| 5,575,284 A | 11/1996 | Athan et al. |
| 5,575,285 A | 11/1996 | Takanashi et al. |
| 5,577,500 A | 11/1996 | Potratz |
| 5,582,169 A | 12/1996 | Oda et al. |
| 5,584,296 A | 12/1996 | Cui et al. |
| 5,588,425 A | 12/1996 | Sackner et al. |
| 5,588,427 A | 12/1996 | Tien |
| 5,590,652 A | 1/1997 | Inai |
| 5,595,176 A | 1/1997 | Yamaura |
| 5,596,986 A | 1/1997 | Goldfarb |
| 5,611,337 A | 3/1997 | Bukta |
| 5,617,852 A | 4/1997 | MacGregor |
| 5,619,992 A | 4/1997 | Guthrie et al. |
| 5,626,140 A | 5/1997 | Feldman et al. |
| 5,630,413 A | 5/1997 | Thomas et al. |
| 5,632,272 A | 5/1997 | Diab et al. |
| 5,632,273 A | 5/1997 | Suzuki |
| 5,634,459 A | 6/1997 | Gardosi |
| 5,638,593 A | 6/1997 | Gerhardt et al. |
| 5,638,816 A | 6/1997 | Kiani-Azarbayjany et al. |
| 5,638,818 A | 6/1997 | Diab et al. |
| 5,645,060 A | 7/1997 | Yorkey et al. |
| 5,645,440 A | 7/1997 | Tobler et al. |
| 5,660,567 A | 8/1997 | Nierlich et al. |
| 5,662,105 A | 9/1997 | Tien |
| 5,662,106 A | 9/1997 | Swedlow et al. |
| 5,664,270 A | 9/1997 | Bell et al. |
| 5,666,952 A | 9/1997 | Fuse et al. |
| 5,671,529 A | 9/1997 | Nelson |
| 5,673,692 A | 10/1997 | Schulze et al. |
| 5,673,693 A | 10/1997 | Solenberger |
| 5,676,139 A | 10/1997 | Goldberger et al. |
| 5,676,141 A | 10/1997 | Hollub |
| 5,678,544 A | 10/1997 | DeLonzor et al. |
| 5,680,857 A | 10/1997 | Pelikan et al. |
| 5,685,299 A | 11/1997 | Diab et al. |
| 5,685,301 A | 11/1997 | Klomhaus |
| 5,687,719 A | 11/1997 | Sato et al. |
| 5,687,722 A | 11/1997 | Tien et al. |
| 5,692,503 A | 12/1997 | Kuenstner |
| 5,692,505 A | 12/1997 | Fouts |
| 5,709,205 A | 1/1998 | Bukta |
| 5,713,355 A | 2/1998 | Richardson et al. |
| 5,724,967 A | 3/1998 | Venkatachalam |
| 5,727,547 A | 3/1998 | Levinson et al. |
| 5,730,124 A | 3/1998 | Yamauchi |
| 5,731,582 A | 3/1998 | West |
| D393,830 S | 4/1998 | Tobler et al. |
| 5,743,260 A | 4/1998 | Chung et al. |
| 5,743,262 A | 4/1998 | Lepper, Jr. et al. |
| 5,743,263 A | 4/1998 | Baker, Jr. |
| 5,746,206 A | 5/1998 | Mannheimer |
| 5,746,697 A | 5/1998 | Swedlow et al. |
| 5,752,914 A | 5/1998 | DeLonzor et al. |
| 5,755,226 A | 5/1998 | Carim et al. |
| 5,758,644 A | 6/1998 | Diab et al. |
| 5,760,910 A | 6/1998 | Lepper, Jr. et al. |
| 5,766,125 A | 6/1998 | Aoyagi et al. |
| 5,766,127 A | 6/1998 | Pologe et al. |
| 5,769,785 A | 6/1998 | Diab et al. |

| | | | | | |
|---|---|---|---|---|---|
| 5,772,587 A | 6/1998 | Gratton et al. | 5,934,277 A | 8/1999 | Mortz |
| 5,774,213 A | 6/1998 | Trebino et al. | 5,934,925 A | 8/1999 | Tobler et al. |
| 5,776,058 A | 7/1998 | Levinson et al. | 5,940,182 A | 8/1999 | Lepper, Jr. et al. |
| 5,776,059 A | 7/1998 | Kaestle | 5,954,644 A | 9/1999 | Dettling et al. |
| 5,779,630 A | 7/1998 | Fein et al. | 5,957,840 A | 9/1999 | Terasawa et al. |
| 5,779,631 A | 7/1998 | Chance | 5,960,610 A | 10/1999 | Levinson et al. |
| 5,782,237 A | 7/1998 | Casciani et al. | 5,961,450 A | 10/1999 | Merchant et al. |
| 5,782,756 A | 7/1998 | Mannheimer | 5,961,452 A | 10/1999 | Chung et al. |
| 5,782,757 A | 7/1998 | Diab et al. | 5,964,701 A | 10/1999 | Asada et al. |
| 5,782,758 A | 7/1998 | Ausec et al. | 5,971,930 A | 10/1999 | Elghazzawi |
| 5,786,592 A | 7/1998 | Hök | 5,978,691 A | 11/1999 | Mills |
| 5,788,634 A | 8/1998 | Suda et al. | 5,978,693 A | 11/1999 | Hamilton et al. |
| 5,790,729 A | 8/1998 | Pologe et al. | 5,983,120 A | 11/1999 | Groner et al. |
| 5,792,052 A | 8/1998 | Issacson et al. | 5,983,122 A | 11/1999 | Jarman et al. |
| 5,795,292 A | 8/1998 | Lewis et al. | 5,987,343 A | 11/1999 | Kinast |
| 5,797,841 A | 8/1998 | DeLonzor et al. | 5,991,648 A | 11/1999 | Levin |
| 5,800,348 A | 9/1998 | Kaestle | 5,995,855 A | 11/1999 | Kiani et al. |
| 5,800,349 A | 9/1998 | Isaacson et al. | 5,995,856 A | 11/1999 | Mannheimer et al. |
| 5,803,910 A | 9/1998 | Potratz | 5,995,858 A | 11/1999 | Kinast |
| 5,807,246 A | 9/1998 | Sakaguchi et al. | 5,995,859 A | 11/1999 | Takahashi |
| 5,807,247 A | 9/1998 | Merchant et al. | 5,997,343 A | 12/1999 | Mills et al. |
| 5,807,248 A | 9/1998 | Mills | 5,999,834 A | 12/1999 | Wang et al. |
| 5,810,723 A | 9/1998 | Aldrich | 6,002,952 A | 12/1999 | Diab et al. |
| 5,810,724 A | 9/1998 | Gronvall | 6,005,658 A | 12/1999 | Kaluza et al. |
| 5,813,980 A | 9/1998 | Levinson et al. | 6,006,120 A | 12/1999 | Levin |
| 5,817,008 A | 10/1998 | Rafert et al. | 6,011,985 A | 1/2000 | Athan et al. |
| 5,817,009 A | 10/1998 | Rosenheimer et al. | 6,011,986 A | 1/2000 | Diab et al. |
| 5,817,010 A | 10/1998 | Hibl | 6,014,576 A | 1/2000 | Raley |
| 5,818,985 A | 10/1998 | Merchant et al. | 6,018,673 A | 1/2000 | Chin et al. |
| 5,820,550 A | 10/1998 | Polson et al. | 6,018,674 A | 1/2000 | Aronow |
| 5,823,950 A | 10/1998 | Diab et al. | 6,022,321 A | 2/2000 | Amano et al. |
| 5,823,952 A | 10/1998 | Levinson et al. | 6,023,541 A | 2/2000 | Merchant et al. |
| 5,827,179 A | 10/1998 | Lichter et al. | 6,026,312 A | 2/2000 | Shemwell et al. |
| 5,827,182 A | 10/1998 | Raley et al. | 6,026,314 A | 2/2000 | Amerov et al. |
| 5,829,439 A | 11/1998 | Yokosawa et al. | 6,031,603 A | 2/2000 | Fine et al. |
| 5,830,135 A | 11/1998 | Bosque et al. | 6,035,223 A | 3/2000 | Baker, Jr. |
| 5,830,136 A | 11/1998 | DeLonzor et al. | 6,036,642 A | 3/2000 | Diab et al. |
| 5,830,137 A | 11/1998 | Scharf | 6,041,247 A | 3/2000 | Weckstrom et al. |
| 5,839,439 A | 11/1998 | Nierlich et al. | 6,044,283 A | 3/2000 | Fein et al. |
| RE36,000 E | 12/1998 | Swedlow et al. | 6,047,201 A | 4/2000 | Jackson, III |
| 5,842,979 A | 12/1998 | Jarman | 6,055,447 A | 4/2000 | Weil |
| 5,842,981 A | 12/1998 | Larsen et al. | 6,061,584 A | 5/2000 | Lovejoy et al. |
| 5,842,982 A | 12/1998 | Mannheimer | 6,064,898 A | 5/2000 | Aldrich |
| 5,846,190 A | 12/1998 | Woehrle | 6,064,899 A | 5/2000 | Fein et al. |
| 5,851,178 A | 12/1998 | Aronow | 6,067,462 A | 5/2000 | Diab et al. |
| 5,851,179 A | 12/1998 | Ritson et al. | 6,073,038 A | 6/2000 | Wang et al. |
| 5,853,364 A | 12/1998 | Baker, Jr. et al. | 6,078,829 A | 6/2000 | Uchida |
| 5,860,919 A | 1/1999 | Kiani-Azarbayjany et al. | 6,078,833 A | 6/2000 | Hueber |
| 5,865,736 A | 2/1999 | Baker, Jr. et al. | 6,081,735 A | 6/2000 | Diab et al. |
| 5,879,294 A | 3/1999 | Anderson et al. | 6,083,157 A | 7/2000 | Noller |
| 5,885,213 A | 3/1999 | Richardson et al. | 6,083,172 A | 7/2000 | Baker, Jr. et al. |
| 5,890,929 A | 4/1999 | Mills et al. | 6,088,607 A | 7/2000 | Diab et al. |
| 5,891,021 A | 4/1999 | Dillon et al. | 6,094,592 A | 7/2000 | Yorkey et al. |
| 5,891,022 A | 4/1999 | Pologe | 6,095,974 A | 8/2000 | Shemwell et al. |
| 5,891,024 A | 4/1999 | Jarman et al. | 6,104,938 A | 8/2000 | Huiku et al. |
| 5,891,025 A | 4/1999 | Buschmann et al. | 6,104,939 A | 8/2000 | Groner |
| 5,891,026 A | 4/1999 | Wang et al. | 6,112,107 A | 8/2000 | Hannula |
| 5,902,235 A | 5/1999 | Lewis et al. | 6,113,541 A | 9/2000 | Dias et al. |
| 5,910,108 A | 6/1999 | Solenberger | 6,115,621 A | 9/2000 | Chin |
| 5,911,690 A | 6/1999 | Rall | 6,122,535 A | 9/2000 | Kaestle et al. |
| 5,912,656 A | 6/1999 | Tham et al. | 6,133,994 A | 10/2000 | Mathews et al. |
| 5,913,819 A | 6/1999 | Taylor et al. | 6,135,952 A | 10/2000 | Coetzee |
| 5,916,154 A | 6/1999 | Hobbs et al. | 6,144,444 A | 11/2000 | Haworth et al. |
| 5,916,155 A | 6/1999 | Levinson et al. | 6,144,867 A | 11/2000 | Walker et al. |
| 5,919,133 A | 7/1999 | Taylor et al. | 6,144,868 A | 11/2000 | Parker |
| 5,919,134 A | 7/1999 | Diab | 6,149,481 A | 11/2000 | Wang et al. |
| 5,920,263 A | 7/1999 | Huttenhoff et al. | 6,151,107 A | 11/2000 | Schöllerman et al. |
| 5,921,921 A | 7/1999 | Potratz et al. | 6,151,516 A | 11/2000 | Kiani-Azarbayjany et al. |
| 5,922,607 A | 7/1999 | Bernreuter | 6,151,518 A | 11/2000 | Hayashi |
| 5,924,979 A | 7/1999 | Swedlow et al. | 6,152,754 A | 11/2000 | Gerhardt et al. |
| 5,924,980 A | 7/1999 | Coetzee | 6,154,667 A | 11/2000 | Miura |
| 5,924,982 A | 7/1999 | Chin | 6,157,850 A | 12/2000 | Diab et al. |
| 5,924,985 A | 7/1999 | Jones | 6,159,147 A | 12/2000 | Lichter |

| | | | | | |
|---|---|---|---|---|---|
| 6,163,715 A | 12/2000 | Larsen et al. | 6,397,092 B1 | 5/2002 | Norris et al. |
| 6,165,005 A | 12/2000 | Mills et al. | 6,397,093 B1 | 5/2002 | Aldrich |
| 6,173,196 B1 | 1/2001 | Delonzor et al. | 6,400,971 B1 | 6/2002 | Finarov et al. |
| 6,178,343 B1 | 1/2001 | Bindszus et al. | 6,400,972 B1 | 6/2002 | Fine |
| 6,179,159 B1 | 1/2001 | Gurley | 6,400,973 B1 | 6/2002 | Winter |
| 6,181,958 B1 | 1/2001 | Steuer et al. | 6,402,690 B1 | 6/2002 | Rhee et al. |
| 6,181,959 B1 | 1/2001 | Schollermann | 6,408,198 B1 | 6/2002 | Hanna et al. |
| 6,184,521 B1 | 2/2001 | Coffin | 6,411,832 B1 | 6/2002 | Guthermann |
| 6,188,470 B1 | 2/2001 | Grace | 6,411,833 B1 | 6/2002 | Baker, Jr. et al. |
| 6,192,260 B1 | 2/2001 | Chance | 6,421,549 B1 | 7/2002 | Jacques |
| 6,195,575 B1 | 2/2001 | Levinson | 6,430,423 B2 | 8/2002 | DeLonzor et al. |
| 6,198,951 B1 | 3/2001 | Kosuda et al. | 6,430,513 B1 | 8/2002 | Wang et al. |
| 6,206,830 B1 | 3/2001 | Diab | 6,430,525 B1 | 8/2002 | Weber |
| 6,213,952 B1 | 4/2001 | Finarov | 6,434,408 B1 | 8/2002 | Heckel et al. |
| 6,217,523 B1 | 4/2001 | Amano et al. | 6,438,396 B1 | 8/2002 | Cook |
| 6,222,189 B1 | 4/2001 | Misner et al. | 6,438,399 B1 | 8/2002 | Kurth |
| 6,223,064 B1 | 4/2001 | Lynn | 6,449,501 B1 | 9/2002 | Reuss |
| 6,226,539 B1 | 5/2001 | Potratz | 6,453,183 B1 | 9/2002 | Walker |
| 6,226,540 B1 | 5/2001 | Bernreuter et al. | 6,453,184 B1 | 9/2002 | Hyogo et al. |
| 6,229,856 B1 | 5/2001 | Diab | 6,456,862 B2 | 9/2002 | Benni |
| 6,230,035 B1 | 5/2001 | Aoyagi et al. | 6,461,305 B1 | 10/2002 | Schnall |
| 6,233,470 B1 | 5/2001 | Tsuchiya | 6,463,310 B1 | 10/2002 | Swedlow et al. |
| 6,236,871 B1 | 5/2001 | Tsuchiya | 6,463,311 B1 | 10/2002 | Diab |
| 6,236,872 B1 | 5/2001 | Diab | 6,466,808 B1 | 10/2002 | Chin et al. |
| 6,240,305 B1 | 5/2001 | Tsuchiya | 6,466,809 B1 | 10/2002 | Riley |
| 6,253,097 B1 | 6/2001 | Aronow | 6,470,199 B1 | 10/2002 | Kopotic |
| 6,253,098 B1 | 6/2001 | Walker et al. | 6,470,200 B2 | 10/2002 | Walker et al. |
| 6,256,523 B1 | 7/2001 | Diab | 6,480,729 B2 | 11/2002 | Stone |
| 6,256,524 B1 | 7/2001 | Walker et al. | 6,490,466 B1 | 12/2002 | Fein et al. |
| 6,261,236 B1 | 7/2001 | Grimblatov | 6,493,568 B1 | 12/2002 | Bell |
| 6,263,221 B1 | 7/2001 | Chance et al. | 6,496,711 B1 | 12/2002 | Athan et al. |
| 6,263,222 B1 | 7/2001 | Diab | 6,498,942 B1 | 12/2002 | Esenaliev et al. |
| 6,263,223 B1 | 7/2001 | Sheperd et al. | 6,501,974 B2 | 12/2002 | Huiku |
| 6,266,546 B1 | 7/2001 | Steuer et al. | 6,501,975 B2 | 12/2002 | Diab |
| 6,266,547 B1 | 7/2001 | Walker et al. | 6,505,060 B1 | 1/2003 | Norris |
| 6,272,363 B1 | 8/2001 | Casciani et al. | 6,505,061 B2 | 1/2003 | Larson |
| 6,278,522 B1 | 8/2001 | Lepper, Jr. | 6,505,133 B1 | 1/2003 | Hanna et al. |
| 6,280,213 B1 | 8/2001 | Tobler | 6,510,329 B2 | 1/2003 | Heckel |
| 6,280,381 B1 | 8/2001 | Malin et al. | 6,510,331 B1 | 1/2003 | Williams et al. |
| 6,285,894 B1 | 9/2001 | Oppelt et al. | 6,512,937 B2 | 1/2003 | Blank et al. |
| 6,285,895 B1 | 9/2001 | Ristolainen et al. | 6,515,273 B2 | 2/2003 | Al-Ali |
| 6,285,896 B1 | 9/2001 | Tobler | 6,519,484 B1 | 2/2003 | Lovejoy et al. |
| 6,298,252 B1 | 10/2001 | Kovach et al. | 6,519,486 B1 | 2/2003 | Edgar, Jr. et al. |
| 6,308,089 B1 | 10/2001 | Von der Ruhr et al. | 6,519,487 B1 | 2/2003 | Parker |
| 6,321,100 B1 | 11/2001 | Parker | 6,525,386 B1 | 2/2003 | Mills |
| 6,330,468 B1 | 12/2001 | Scharf | 6,526,300 B1 | 2/2003 | Kiani |
| 6,334,065 B1 | 12/2001 | Al-Ali | 6,526,301 B2 | 2/2003 | Larsen et al. |
| 6,339,715 B1 | 1/2002 | Bahr et al. | 6,541,756 B2 | 4/2003 | Schulz |
| 6,342,039 B1 | 1/2002 | Lynn | 6,542,764 B1 | 4/2003 | Al-Ali |
| 6,343,223 B1 | 1/2002 | Chin et al. | 6,546,267 B1 | 4/2003 | Sugiura et al. |
| 6,343,224 B1 | 1/2002 | Parker | 6,553,241 B2 | 4/2003 | Mannheimer et al. |
| 6,349,228 B1 | 2/2002 | Kiani | 6,553,242 B1 | 4/2003 | Sarussi |
| 6,351,658 B1 | 2/2002 | Middleman et al. | 6,553,243 B2 | 4/2003 | Gurley |
| 6,353,750 B1 | 3/2002 | Kimura | 6,554,788 B1 | 4/2003 | Hunley |
| 6,356,774 B1 | 3/2002 | Bernstein et al. | 6,556,852 B1 | 4/2003 | Schulze et al. |
| 6,360,113 B1 | 3/2002 | Dettling | 6,560,470 B1 | 5/2003 | Pologe |
| 6,360,114 B1 | 3/2002 | Diab | 6,564,077 B2 | 5/2003 | Mortara |
| 6,361,501 B1 | 3/2002 | Amano et al. | 6,564,088 B1 | 5/2003 | Soller et al. |
| 6,363,269 B1 | 3/2002 | Hanna et al. | 6,571,113 B1 | 5/2003 | Fein et al. |
| D455,834 S | 4/2002 | Donars et al. | 6,571,114 B1 | 5/2003 | Koike et al. |
| 6,370,408 B1 | 4/2002 | Merchant et al. | 6,574,491 B2 | 6/2003 | Elghazzawi |
| 6,370,409 B1 | 4/2002 | Chung et al. | 6,580,086 B1 | 6/2003 | Schulz |
| 6,371,921 B1 | 4/2002 | Caro | 6,584,336 B1 | 6/2003 | Al-Ali |
| 6,374,129 B1 | 4/2002 | Chin | 6,587,703 B2 | 7/2003 | Cheng et al. |
| 6,377,829 B1 | 4/2002 | Al-Ali | 6,587,704 B1 | 7/2003 | Fine et al. |
| 6,381,479 B1 | 4/2002 | Norris | 6,589,172 B2 | 7/2003 | Williams et al. |
| 6,381,480 B1 | 4/2002 | Stoddar et al. | 6,591,122 B2 | 7/2003 | Schmitt |
| 6,385,471 B1 | 5/2002 | Mortz | 6,591,123 B2 | 7/2003 | Fein et al. |
| 6,385,821 B1 | 5/2002 | Modgil et al. | 6,594,511 B2 | 7/2003 | Stone et al. |
| 6,388,240 B2 | 5/2002 | Schulz | 6,594,512 B2 | 7/2003 | Huang |
| 6,393,310 B1 | 5/2002 | Kuenster | 6,594,513 B1 | 7/2003 | Jobsis et al. |
| 6,393,311 B1 | 5/2002 | Edgar, Jr. et al. | 6,597,931 B1 | 7/2003 | Cheng et al. |
| 6,397,091 B2 | 5/2002 | Diab | 6,597,933 B2 | 7/2003 | Kiani |

| | | |
|---|---|---|
| 6,600,940 B1 | 7/2003 | Fein et al. |
| 6,606,510 B2 | 8/2003 | Swedlow et al. |
| 6,606,511 B1 | 8/2003 | Al-Ali |
| 6,606,512 B2 | 8/2003 | Muz et al. |
| 6,609,016 B1 | 8/2003 | Lynn |
| 6,615,064 B1 | 9/2003 | Aldrich |
| 6,615,065 B1 | 9/2003 | Barrett et al. |
| 6,618,602 B2 | 9/2003 | Levin |
| 6,622,034 B1 | 9/2003 | Gorski et al. |
| 6,628,975 B1 | 9/2003 | Fein et al. |
| 6,631,281 B1 | 10/2003 | Kästle |
| 6,632,181 B2 | 10/2003 | Flaherty |
| 6,640,116 B2 | 10/2003 | Diab |
| 6,643,530 B2 | 11/2003 | Diab |
| 6,643,531 B1 | 11/2003 | Katarow |
| 6,647,279 B2 | 11/2003 | Pologue |
| 6,647,280 B2 | 11/2003 | Bahr et al. |
| 6,650,916 B2 | 11/2003 | Cook |
| 6,650,917 B2 | 11/2003 | Diab |
| 6,650,918 B2 | 11/2003 | Terry |
| 6,654,621 B2 | 11/2003 | Palatnik |
| 6,654,622 B1 | 11/2003 | Eberhard et al. |
| 6,654,623 B1 | 11/2003 | Kästle |
| 6,654,624 B2 | 11/2003 | Diab |
| 6,658,277 B2 | 12/2003 | Wasserman |
| 6,658,279 B2 | 12/2003 | Swanson et al. |
| 6,662,033 B2 | 12/2003 | Casciani et al. |
| 6,665,551 B1 | 12/2003 | Suzuki |
| 6,668,182 B2 | 12/2003 | Hubelbank |
| 6,668,183 B2 | 12/2003 | Hicks et al. |
| 6,671,526 B1 | 12/2003 | Aoyagi et al. |
| 6,671,528 B2 | 12/2003 | Steuer et al. |
| 6,671,530 B2 | 12/2003 | Chung et al. |
| 6,671,531 B2 | 12/2003 | Al-Ali |
| 6,671,532 B1 | 12/2003 | Fudge et al. |
| 6,675,031 B1 | 1/2004 | Porges et al. |
| 6,678,543 B2 | 1/2004 | Diab |
| 6,681,126 B2 | 1/2004 | Solenberger |
| 6,681,128 B2 | 1/2004 | Steuer et al. |
| 6,681,454 B2 | 1/2004 | Modgil et al. |
| 6,684,090 B2 | 1/2004 | Ali et al. |
| 6,684,091 B2 | 1/2004 | Parker |
| 6,694,160 B2 | 2/2004 | Chin |
| 6,697,653 B2 | 2/2004 | Hanna |
| 6,697,655 B2 | 2/2004 | Sueppel et al. |
| 6,697,656 B1 | 2/2004 | Al-Ali |
| 6,697,658 B2 | 2/2004 | Al-Ali |
| RE38,476 E | 3/2004 | Diab et al. |
| 6,699,194 B1 | 3/2004 | Diab |
| 6,699,199 B2 | 3/2004 | Asada et al. |
| 6,701,170 B2 | 3/2004 | Stetson |
| 6,702,752 B2 | 3/2004 | Dekker |
| 6,707,257 B2 | 3/2004 | Norris |
| 6,708,049 B1 | 3/2004 | Berson et al. |
| 6,709,402 B2 | 3/2004 | Dekker |
| 6,711,424 B1 | 3/2004 | Fine et al. |
| 6,711,425 B1 | 3/2004 | Reuss |
| 6,712,762 B1 | 3/2004 | Lichter |
| 6,714,803 B1 | 3/2004 | Mortz |
| 6,714,804 B2 | 3/2004 | Al-Ali |
| 6,714,805 B2 | 3/2004 | Jeon et al. |
| RE38,492 E | 4/2004 | Diab et al. |
| 6,719,686 B2 | 4/2004 | Coakley et al. |
| 6,719,705 B2 | 4/2004 | Mills |
| 6,720,734 B2 | 4/2004 | Norris |
| 6,721,584 B2 | 4/2004 | Baker, Jr. et al. |
| 6,721,585 B1 | 4/2004 | Parker |
| 6,725,074 B1 | 4/2004 | Kästle |
| 6,725,075 B2 | 4/2004 | Al-Ali |
| 6,731,962 B1 | 5/2004 | Katarow |
| 6,731,963 B2 | 5/2004 | Finarov et al. |
| 6,731,967 B1 | 5/2004 | Turcott |
| 6,735,459 B2 | 5/2004 | Parker |
| 6,745,060 B2 | 6/2004 | Diab et al. |
| 6,745,061 B1 | 6/2004 | Hicks et al. |
| 6,748,253 B2 | 6/2004 | Norris et al. |
| 6,748,254 B2 | 6/2004 | O'Neill et al. |
| 6,754,515 B1 | 6/2004 | Pologe |
| 6,754,516 B2 | 6/2004 | Mannheimer |
| 6,760,607 B2 | 7/2004 | Al-Ali |
| 6,760,609 B2 | 7/2004 | Jacques |
| 6,760,610 B2 | 7/2004 | Tscupp et al. |
| 6,763,255 B2 | 7/2004 | DeLonzor et al. |
| 6,763,256 B2 | 7/2004 | Kimball et al. |
| 6,770,028 B1 | 8/2004 | Ali et al. |
| 6,771,994 B2 | 8/2004 | Kiani et al. |
| 6,773,397 B2 | 8/2004 | Kelly |
| 6,778,923 B2 | 8/2004 | Norris et al. |
| 6,780,158 B2 | 8/2004 | Yarita |
| 6,791,689 B1 | 9/2004 | Weckstrom |
| 6,792,300 B1 | 9/2004 | Diab |
| 6,801,797 B2 | 10/2004 | Mannheimer et al. |
| 6,801,798 B2 | 10/2004 | Geddes et al. |
| 6,801,799 B2 | 10/2004 | Mendelson |
| 6,801,802 B2 | 10/2004 | Sitzman et al. |
| 6,802,812 B1 | 10/2004 | Walker et al. |
| 6,805,673 B2 | 10/2004 | Dekker |
| 6,810,277 B2 | 10/2004 | Edgar, Jr. et al. |
| 6,813,511 B2 | 11/2004 | Diab |
| 6,816,741 B2 | 11/2004 | Diab |
| 6,819,950 B2 | 11/2004 | Mills |
| 6,822,564 B2 | 11/2004 | Al-Ali |
| 6,825,619 B2 | 11/2004 | Norris |
| 6,826,419 B2 | 11/2004 | Diab et al. |
| 6,829,496 B2 | 12/2004 | Nagai et al. |
| 6,830,711 B2 | 12/2004 | Mills |
| 6,836,679 B2 | 12/2004 | Baker, Jr. et al. |
| 6,839,579 B1 | 1/2005 | Chin |
| 6,839,580 B2 | 1/2005 | Zonios et al. |
| 6,839,582 B2 | 1/2005 | Heckel |
| 6,839,659 B2 | 1/2005 | Tarassenko et al. |
| 6,842,635 B1 | 1/2005 | Parker |
| 6,845,256 B2 | 1/2005 | Chin |
| 6,850,787 B2 | 2/2005 | Weber et al. |
| 6,850,788 B2 | 2/2005 | Al-Ali |
| 6,850,789 B2 | 2/2005 | Schweitzer, Jr. et al. |
| 6,861,639 B2 | 3/2005 | Al-Ali |
| 6,863,652 B2 | 3/2005 | Huang et al. |
| 6,865,407 B2 | 3/2005 | Kimball et al. |
| 6,879,850 B2 | 4/2005 | Kimball |
| 6,882,874 B2 | 4/2005 | Huiku |
| 6,898,452 B2 | 5/2005 | Al-Ali et al. |
| 6,909,912 B2 | 6/2005 | Melker |
| 6,912,413 B2 | 6/2005 | Rantala et al. |
| 6,916,289 B2 | 7/2005 | Schnall |
| 6,920,345 B2 | 7/2005 | Al-Ali et al. |
| 6,931,269 B2 | 8/2005 | Terry |
| 6,934,570 B2 | 8/2005 | Kiani et al. |
| 6,941,162 B2 | 9/2005 | Fudge et al. |
| 6,947,781 B2 | 9/2005 | Asada et al. |
| 6,950,687 B2 | 9/2005 | Al-Ali |
| 6,954,664 B2 | 10/2005 | Sweitzer |
| 6,963,767 B2 | 11/2005 | Rantala et al. |
| 6,968,221 B2 | 11/2005 | Rosenthal |
| 6,971,580 B2 | 12/2005 | DeLonzor et al. |
| 6,979,812 B2 | 12/2005 | Al-Ali |
| 6,983,178 B2 | 1/2006 | Fine |
| 6,985,763 B2 | 1/2006 | Boas et al. |
| 6,985,764 B2 | 1/2006 | Mason |
| 6,990,426 B2 | 1/2006 | Yoon et al. |
| 6,992,751 B2 | 1/2006 | Al-Ali |
| 6,992,772 B2 | 1/2006 | Block et al. |
| 6,993,371 B2 | 1/2006 | Kiani et al. |
| 6,993,372 B2 | 1/2006 | Fine et al. |
| 6,996,427 B2 | 2/2006 | Ali et al. |
| 7,003,338 B2 | 2/2006 | Weber et al. |

| Patent/Pub. No. | Date | Name |
|---|---|---|
| 7,003,339 B2 | 2/2006 | Diab et al. |
| 7,006,855 B1 | 2/2006 | Sarussi |
| 7,006,856 B2 | 2/2006 | Baker, Jr. et al. |
| 7,016,715 B2 | 3/2006 | Stetson |
| 7,020,507 B2 | 3/2006 | Scharf et al. |
| 7,024,233 B2 | 4/2006 | Ali et al. |
| 7,024,235 B2 | 4/2006 | Melker |
| 7,025,728 B2 | 4/2006 | Ito et al. |
| 7,027,849 B2 | 4/2006 | Al-Ali et al. |
| 7,027,850 B2 | 4/2006 | Wasserman |
| 7,039,449 B2 | 5/2006 | Al-Ali |
| 7,043,289 B2 | 5/2006 | Fine et al. |
| 7,047,055 B2 | 5/2006 | Boaz et al. |
| 7,060,035 B2 | 6/2006 | Wasserman et al. |
| 7,062,307 B2 | 6/2006 | Norris et al. |
| 7,067,893 B2 | 6/2006 | Mills |
| 7,072,701 B2 | 7/2006 | Chen et al. |
| 7,072,702 B2 | 7/2006 | Edgar, Jr. et al. |
| 7,079,880 B2 | 7/2006 | Stetson |
| 7,085,597 B2 | 8/2006 | Fein et al. |
| 7,096,052 B2 | 8/2006 | Mason et al. |
| 7,096,054 B2 | 8/2006 | Abdul-Hafiz et al. |
| 7,107,088 B2 | 9/2006 | Aceti |
| 7,113,815 B2 | 9/2006 | O'Neil et al. |
| 7,123,950 B2 | 10/2006 | Mannheimer |
| 7,127,278 B2 | 10/2006 | Melker |
| 7,130,671 B2 | 10/2006 | Baker, Jr. et al. |
| 7,132,641 B2 | 11/2006 | Schulz |
| 7,133,711 B2 | 11/2006 | Chernoguz et al. |
| 7,139,599 B2 | 11/2006 | Terry |
| 7,142,901 B2 | 11/2006 | Kiani et al. |
| 7,162,288 B2 | 1/2007 | Nordstrom |
| 7,190,987 B2 | 3/2007 | Lindekugel et al. |
| 7,198,778 B2 | 4/2007 | Mannheimer et al. |
| 7,215,984 B2 | 5/2007 | Diab et al. |
| 7,225,006 B2 | 5/2007 | Al-Ali et al. |
| 7,228,161 B2 | 6/2007 | Chin |
| 7,236,811 B2 | 6/2007 | Schmitt et al. |
| 7,248,910 B2 | 7/2007 | Li et al. |
| 7,254,433 B2 | 8/2007 | Diab et al. |
| 7,254,434 B2 | 8/2007 | Schulz et al. |
| 7,280,858 B2 | 10/2007 | Al-Ali et al. |
| 7,295,866 B2 | 11/2007 | Al-Ali et al. |
| 7,305,262 B2 | 12/2007 | Brodnick et al. |
| 7,315,753 B2 | 1/2008 | Baker, Jr. et al. |
| 7,412,272 B2 | 8/2008 | Medina |
| 2001/0021803 A1 | 9/2001 | Blank et al. |
| 2001/0051767 A1 | 12/2001 | Williams et al. |
| 2002/0016537 A1 | 2/2002 | Muz et al. |
| 2002/0026109 A1 | 2/2002 | Diab et al. |
| 2002/0028990 A1 | 3/2002 | Shepherd et al. |
| 2002/0038078 A1 | 3/2002 | Ito |
| 2002/0042558 A1 | 4/2002 | Mendelson |
| 2002/0068859 A1 | 6/2002 | Knopp |
| 2002/0072681 A1 | 6/2002 | Schnall |
| 2002/0116797 A1 | 8/2002 | Modgil et al. |
| 2002/0128544 A1 | 9/2002 | Diab et al. |
| 2002/0133067 A1 | 9/2002 | Jackson, III |
| 2002/0156354 A1 | 10/2002 | Larson |
| 2002/0173706 A1 | 11/2002 | Takatani |
| 2002/0173709 A1 | 11/2002 | Fine et al. |
| 2002/0190863 A1 | 12/2002 | Lynn |
| 2002/0198442 A1 | 12/2002 | Rantala et al. |
| 2003/0018243 A1 | 1/2003 | Gerhardt et al. |
| 2003/0036690 A1 | 2/2003 | Geddes et al. |
| 2003/0045785 A1 | 3/2003 | Diab et al. |
| 2003/0073889 A1 | 4/2003 | Keilbach et al. |
| 2003/0073890 A1 | 4/2003 | Hanna |
| 2003/0100840 A1 | 5/2003 | Sugiura et al. |
| 2003/0132495 A1 | 7/2003 | Mills et al. |
| 2003/0135099 A1 | 7/2003 | Al-Ali |
| 2003/0162414 A1 | 8/2003 | Schulz et al. |
| 2003/0171662 A1 | 9/2003 | O'Connor et al. |
| 2003/0176776 A1 | 9/2003 | Huiku |
| 2003/0181799 A1 | 9/2003 | Lindekugel et al. |
| 2003/0187337 A1 | 10/2003 | Tarassenko et al. |
| 2003/0195402 A1 | 10/2003 | Fein et al. |
| 2003/0197679 A1 | 10/2003 | Ali et al. |
| 2003/0212316 A1 | 11/2003 | Leiden |
| 2003/0225323 A1 | 12/2003 | Kiani et al. |
| 2003/0225337 A1 | 12/2003 | Scharf et al. |
| 2003/0236452 A1 | 12/2003 | Melker et al. |
| 2003/0236647 A1 | 12/2003 | Yoon et al. |
| 2004/0006261 A1 | 1/2004 | Swedlow et al. |
| 2004/0010188 A1 | 1/2004 | Wasserman et al. |
| 2004/0024297 A1 | 2/2004 | Chen et al. |
| 2004/0024326 A1 | 2/2004 | Yeo et al. |
| 2004/0034293 A1 | 2/2004 | Kimball |
| 2004/0039272 A1 | 2/2004 | Abdul-Hafiz et al. |
| 2004/0039273 A1 | 2/2004 | Terry |
| 2004/0054269 A1 | 3/2004 | Rantala et al. |
| 2004/0054291 A1 | 3/2004 | Schulz |
| 2004/0059209 A1 | 3/2004 | Al-Ali et al. |
| 2004/0059210 A1 | 3/2004 | Stetson |
| 2004/0064020 A1 | 4/2004 | Diab et al. |
| 2004/0068164 A1 | 4/2004 | Diab et al. |
| 2004/0087846 A1 | 5/2004 | Wasserman |
| 2004/0092805 A1 | 5/2004 | Yarita |
| 2004/0097797 A1 | 5/2004 | Porges et al. |
| 2004/0098009 A1 | 5/2004 | Boecker et al. |
| 2004/0107065 A1 | 6/2004 | Al-Ali et al. |
| 2004/0116788 A1 | 6/2004 | Chernoguz et al. |
| 2004/0116789 A1 | 6/2004 | Boaz et al. |
| 2004/0117891 A1 | 6/2004 | Hannula et al. |
| 2004/0122300 A1 | 6/2004 | Boas et al. |
| 2004/0122302 A1 | 6/2004 | Mason et al. |
| 2004/0133087 A1 | 7/2004 | Ali et al. |
| 2004/0133088 A1 | 7/2004 | Al-Ali et al. |
| 2004/0138538 A1 | 7/2004 | Stetson |
| 2004/0138540 A1 | 7/2004 | Baker, Jr. et al. |
| 2004/0143172 A1 | 7/2004 | Fudge et al. |
| 2004/0147821 A1 | 7/2004 | Al-Ali et al. |
| 2004/0147822 A1 | 7/2004 | Al-Ali et al. |
| 2004/0147823 A1 | 7/2004 | Kiani et al. |
| 2004/0147824 A1 | 7/2004 | Diab |
| 2004/0152965 A1 | 8/2004 | Diab et al. |
| 2004/0158134 A1 | 8/2004 | Diab et al. |
| 2004/0158135 A1 | 8/2004 | Baker, Jr. et al. |
| 2004/0162472 A1 | 8/2004 | Berson et al. |
| 2004/0167381 A1 | 8/2004 | Lichter |
| 2004/0171920 A1 | 9/2004 | Mannheimer et al. |
| 2004/0171948 A1 | 9/2004 | Terry |
| 2004/0176671 A1 | 9/2004 | Fine et al. |
| 2004/0181133 A1 | 9/2004 | Al-Ali et al. |
| 2004/0181134 A1 | 9/2004 | Baker, Jr. et al. |
| 2004/0186358 A1 | 9/2004 | Chernow et al. |
| 2004/0199063 A1 | 10/2004 | O'Neil et al. |
| 2004/0204636 A1 | 10/2004 | Diab et al. |
| 2004/0204637 A1 | 10/2004 | Diab et al. |
| 2004/0204638 A1 | 10/2004 | Diab et al. |
| 2004/0204639 A1 | 10/2004 | Casciani et al. |
| 2004/0204865 A1 | 10/2004 | Lee et al. |
| 2004/0210146 A1 | 10/2004 | Diab et al. |
| 2004/0215069 A1 | 10/2004 | Mannheimer |
| 2004/0215085 A1 | 10/2004 | Schnall |
| 2004/0230107 A1 | 11/2004 | Asada et al. |
| 2004/0230108 A1 | 11/2004 | Melker et al. |
| 2004/0236196 A1 | 11/2004 | Diab et al. |
| 2004/0242980 A1 | 12/2004 | Kiani et al. |
| 2004/0249252 A1 | 12/2004 | Fine et al. |
| 2004/0257557 A1 | 12/2004 | Block et al. |
| 2004/0260161 A1 | 12/2004 | Melker et al. |
| 2004/0267103 A1 | 12/2004 | Li |
| 2004/0267104 A1 | 12/2004 | Hannula et al. |
| 2004/0267140 A1 | 12/2004 | Ito et al. |
| 2005/0004479 A1 | 1/2005 | Townsend et al. |

| | | | | | | |
|---|---|---|---|---|---|---|
| 2005/0010092 A1 | 1/2005 | Weber et al. | | EP | 0531631 | 9/1992 |
| 2005/0014999 A1 | 1/2005 | Rahe-Meyer | | EP | 0566354 | 4/1993 |
| 2005/0020887 A1 | 1/2005 | Goldberg | | EP | 0587009 | 8/1993 |
| 2005/0020894 A1 | 1/2005 | Norris et al. | | EP | 00630203 | 9/1993 |
| 2005/0033128 A1 | 2/2005 | Ali et al. | | EP | 0 572 684 A1 | 12/1993 |
| 2005/0033129 A1 | 2/2005 | Edgar, Jr. et al. | | EP | 00615723 | 9/1994 |
| 2005/0033131 A1 | 2/2005 | Chen | | EP | 00702931 | 3/1996 |
| 2005/0043599 A1 | 2/2005 | O'Mara | | EP | 00724860 | 8/1996 |
| 2005/0043600 A1 | 2/2005 | Diab | | EP | 00793942 | 9/1997 |
| 2005/0049468 A1 | 3/2005 | Carlson | | EP | 0 864 293 A1 | 9/1998 |
| 2005/0049470 A1 | 3/2005 | Terry | | EP | 01006863 | 10/1998 |
| 2005/0049471 A1 | 3/2005 | Aceti | | EP | 01006864 | 10/1998 |
| 2005/0070773 A1 | 3/2005 | Chin | | EP | 0875199 | 11/1998 |
| 2005/0070775 A1 | 3/2005 | Chin | | EP | 00998214 | 12/1998 |
| 2005/0075546 A1 | 4/2005 | Samsoondar | | EP | 0 898 933 A | 3/1999 |
| 2005/0075550 A1 | 4/2005 | Lindekugel | | EP | 0 898 933 A2 | 3/1999 |
| 2005/0085704 A1 | 4/2005 | Schulz | | EP | 01332713 | 8/2003 |
| 2005/0090720 A1 | 4/2005 | Wu | | EP | 01469773 | 8/2003 |
| 2005/0197548 A1 | 9/2005 | Dietiker | | EP | 1502529 | 7/2004 |
| 2005/0228248 A1 | 10/2005 | Dietiker | | EP | 01491135 | 12/2004 |
| 2005/0234317 A1 | 10/2005 | Kiani | | EP | 1491135 | 12/2004 |
| 2005/0256386 A1 | 11/2005 | Chen | | EP | 1807001 | 7/2007 |
| 2005/0272986 A1 | 12/2005 | Smith | | FR | 2685865 | 1/1992 |
| 2005/0277819 A1 | 12/2005 | Kiani et al. | | GB | 2 259 545 A | 3/1993 |
| 2006/0020179 A1 | 1/2006 | Anderson | | JP | 63275325 | 11/1988 |
| 2006/0030764 A1 | 2/2006 | Porges | | JP | 2013450 | 1/1990 |
| 2006/0058594 A1 | 3/2006 | Ishizuka et al. | | JP | 2111343 | 4/1990 |
| 2006/0074280 A1 | 4/2006 | Martis | | JP | 02-191434 | 7/1990 |
| 2006/0084852 A1 | 4/2006 | Mason et al. | | JP | 2237544 | 9/1990 |
| 2006/0084878 A1 | 4/2006 | Banet | | JP | 03-173536 | 7/1991 |
| 2006/0089547 A1 | 4/2006 | Sarussi | | JP | 3170866 | 7/1991 |
| 2006/0106294 A1 | 5/2006 | Maser et al. | | JP | 3245042 | 10/1991 |
| 2006/0122517 A1 | 6/2006 | Banet | | JP | 4038280 | 3/1992 |
| 2006/0129039 A1 | 6/2006 | Lindner | | JP | 4174648 | 6/1992 |
| 2006/0155198 A1 | 7/2006 | Schmid | | JP | 4191642 | 7/1992 |
| 2006/0173257 A1 | 8/2006 | Nagai | | JP | 4332536 | 11/1992 |
| 2006/0200029 A1 | 9/2006 | Evans et al. | | JP | 3124073 | 3/1993 |
| 2007/0027376 A1 | 2/2007 | Todokoro et al. | | JP | 5049624 | 3/1993 |
| 2007/0078311 A1 | 4/2007 | Al-Ali et al. | | JP | 5049625 | 3/1993 |
| 2007/0197887 A1 | 8/2007 | Lunak et al. | | JP | 3115374 | 4/1993 |
| 2008/0262328 A1 | 10/2008 | Adams | | JP | 05-200031 | 8/1993 |
| | | | | JP | 5212016 | 8/1993 |
| FOREIGN PATENT DOCUMENTS | | | | JP | 06-014906 | 1/1994 |
| DE | 3405444 A1 | 8/1985 | | JP | 6016774 | 3/1994 |
| DE | 3516338 A1 | 11/1986 | | JP | 3116255 | 4/1994 |
| DE | 37 03 458 C2 | 8/1988 | | JP | 6029504 | 4/1994 |
| DE | 3938759 A1 | 5/1991 | | JP | 6098881 | 4/1994 |
| DE | 4210102 | 9/1993 | | JP | 06-154177 | 6/1994 |
| DE | 44 23 597 C1 | 8/1995 | | JP | 6269430 | 9/1994 |
| DE | 4423597 C1 | 8/1995 | | JP | 6285048 | 10/1994 |
| DE | 19632361 A1 | 2/1997 | | JP | 7001273 | 1/1995 |
| DE | 69123448 T2 | 5/1997 | | JP | 7124138 | 5/1995 |
| DE | 19703220 A1 | 7/1997 | | JP | 7136150 | 5/1995 |
| DE | 19640807 | 9/1997 | | JP | 3116259 | 6/1995 |
| DE | 19647877 | 4/1998 | | JP | 3116260 | 6/1995 |
| DE | 100 30 862 | 1/2002 | | JP | 7155311 | 6/1995 |
| DE | 20318882 | 4/2004 | | JP | 7155313 | 6/1995 |
| EP | 0127947 | 5/1984 | | JP | 3238813 | 7/1995 |
| EP | 00194105 | 9/1986 | | JP | 7171139 | 7/1995 |
| EP | 0 204 459 A2 | 12/1986 | | JP | 3134144 | 9/1995 |
| EP | 0204 459 | 12/1986 | | JP | 7236625 | 9/1995 |
| EP | 204459 | 12/1986 | | JP | 7246191 | 9/1995 |
| EP | 0 262 779 A1 | 4/1988 | | JP | 8256996 | 10/1996 |
| EP | 0315040 | 10/1988 | | JP | 9192120 | 7/1997 |
| EP | 0314331 | 5/1989 | | JP | 10216113 | 8/1998 |
| EP | 00352923 | 1/1990 | | JP | 10216114 | 8/1998 |
| EP | 0 360 977 A1 | 4/1990 | | JP | 10216115 | 8/1998 |
| EP | 00430340 | 6/1991 | | JP | 10337282 | 12/1998 |
| EP | 430340 | 6/1991 | | JP | 11019074 | 1/1999 |
| EP | 0435 500 | 7/1991 | | JP | 11155841 | 6/1999 |
| EP | 00497021 | 8/1992 | | JP | 11-188019 | 7/1999 |
| EP | 0529412 | 8/1992 | | JP | 11244268 | 9/1999 |
| | | | | JP | 20107157 | 4/2000 |

| | | |
|---|---|---|
| JP | 20237170 | 9/2000 |
| JP | 21245871 | 9/2001 |
| JP | 22224088 | 8/2002 |
| JP | 22282242 | 10/2002 |
| JP | 23153881 | 5/2003 |
| JP | 23153882 | 5/2003 |
| JP | 23169791 | 6/2003 |
| JP | 23194714 | 7/2003 |
| JP | 23210438 | 7/2003 |
| JP | 23275192 | 9/2003 |
| JP | 23339678 | 12/2003 |
| JP | 24008572 | 1/2004 |
| JP | 24089546 | 3/2004 |
| JP | 24113353 | 4/2004 |
| JP | 24135854 | 5/2004 |
| JP | 24148069 | 5/2004 |
| JP | 24148070 | 5/2004 |
| JP | 24159810 | 6/2004 |
| JP | 24166775 | 6/2004 |
| JP | 24194908 | 7/2004 |
| JP | 24202190 | 7/2004 |
| JP | 24248820 | 9/2004 |
| JP | 24261364 | 9/2004 |
| JP | 24290412 | 10/2004 |
| JP | 24290544 | 10/2004 |
| JP | 24290545 | 10/2004 |
| JP | 24329406 | 11/2004 |
| JP | 24329607 | 11/2004 |
| JP | 24329928 | 11/2004 |
| JP | 24337605 | 12/2004 |
| JP | 24344367 | 12/2004 |
| JP | 24351107 | 12/2004 |
| JP | 25034472 | 2/2005 |
| JP | 25110816 | 4/2005 |
| JP | 26158555 | 6/2006 |
| WO | WO 98/09566 | 10/1989 |
| WO | WO 90/01293 | 2/1990 |
| WO | WO 90/04352 | 5/1990 |
| WO | WO 91/01678 | 2/1991 |
| WO | WO 91/11137 | 8/1991 |
| WO | WO 92/00513 | 1/1992 |
| WO | WO 92/21281 | 12/1992 |
| WO | WO 93/09711 | 5/1993 |
| WO | WO 93/13706 | 7/1993 |
| WO | WO 93/16629 | 9/1993 |
| WO | WO 94/03102 | 2/1994 |
| WO | WO 94/23643 | 10/1994 |
| WO | WO 95/02358 | 1/1995 |
| WO | WO 95/12349 | 5/1995 |
| WO | WO 95/16970 | 6/1995 |
| WO | WO 96/13208 | 5/1996 |
| WO | WO 96/39927 | 12/1996 |
| WO | WO 97/36536 | 10/1997 |
| WO | WO 97/36538 | 10/1997 |
| WO | WO 97/40741 | 11/1997 |
| WO | WO 97/49330 | 12/1997 |
| WO | WO 98/17174 | 4/1998 |
| WO | WO 98/18382 | 5/1998 |
| WO | WO 98/43071 | 10/1998 |
| WO | WO 98/51212 | 11/1998 |
| WO | WO 98/57577 | 12/1998 |
| WO | WO 99/00053 | 1/1999 |
| WO | WO 99/32030 | 7/1999 |
| WO | WO 99/47039 | 9/1999 |
| WO | WO 99/63884 | 12/1999 |
| WO | WO 00/21438 | 4/2000 |
| WO | WO 00/28888 | 5/2000 |
| WO | 0059374 | 10/2000 |
| WO | WO 00/59374 | 10/2000 |
| WO | WO 01/13790 | 3/2001 |
| WO | WO 01/16577 | 3/2001 |
| WO | WO 01/17421 | 3/2001 |
| WO | WO 01/47426 | 3/2001 |
| WO | WO 01/40776 | 6/2001 |
| WO | WO 01/67946 A1 | 9/2001 |
| WO | WO 01/76461 | 10/2001 |
| WO | WO 02/14793 | 2/2002 |
| WO | WO 02/35999 | 5/2002 |
| WO | WO 02/062213 | 8/2002 |
| WO | WO 02/074162 | 9/2002 |
| WO | WO 02/085202 A1 | 10/2002 |
| WO | WO 03/000125 | 1/2003 |
| WO | WO 03/001180 | 1/2003 |
| WO | WO 03/009750 | 2/2003 |
| WO | WO 03/011127 | 2/2003 |
| WO | WO 03/020129 A1 | 3/2003 |
| WO | WO 03/039326 | 5/2003 |
| WO | WO 03/063697 | 8/2003 |
| WO | WO 03/073924 | 9/2003 |
| WO | WO 2004/000114 | 12/2003 |
| WO | WO 2004/006748 | 1/2004 |
| WO | WO 2004/069046 A1 | 8/2004 |
| WO | WO 2004/075746 | 9/2004 |
| WO | WO 2005/002434 | 1/2005 |
| WO | WO 2005/009221 | 2/2005 |
| WO | WO 2005/010567 | 2/2005 |
| WO | WO 2005/010568 | 2/2005 |
| WO | WO 2005/020120 | 3/2005 |
| WO | WO 2005/065540 A1 | 7/2005 |
| WO | 06064399 | 6/2006 |
| WO | WO 2006/104790 | 10/2006 |

OTHER PUBLICATIONS

Johnston, W.S., et al.; "Extracting Breathing Rate Infromation from a Wearable Reflectance Pulse Oximeter Sensor," *Proceedings of the 26th Annual International conference of the IEEE EMBS*, San Francisco, California; Sep. 1-5, 2004; pp. 5388-5391.

Spigulis, Janis, et al.; "Optical multi-channel sensing of skin blood pulsations," *Optical Sensing, Proceedings of SPIE*, vol. 5459, pp. 46-53 (2004).

Yan, Yong-sheng, et al.; "Reduction of motion artifact in pulse oximetry by smoothed pseudo WignerVille distribution," *Journal of NeuroEngineering and Rehabilitation*, vol. 2, No. 3 (9 pages) (Mar. 2005).

Urquhart, C., et al.; "Ear probe pulse oximeters and neonates," *Anaesthesia*, vol. 60, p. 294 (2005).

Jonnson, P.O. "Patent Cooperation Treaty PCT Written Opinion of the International Searching Authority"; Apr. 20, 2007; 12pp.; European Patent Office; Berlin.

Hayoz, J. , et al.; "World's First Combined digital Pulse Oximetry Pulse Oximetry and Carbon Dioxide Tension Ear Sensor", *Abstracts*, A6, p. S103. (undated).

Huang, J., et al.; "Low Power Motion Tolerant Pulse Oximetry," *Abstracts*, A7, p. S 103. (undated).

Lang, P., et al.; "Signal Identification and Quality Indicator™ for Motion Resistant Pulse Oximetry," *Abstracts*, A10, p. S105. (undated).

Neumann, R., et al.; "Fourier Artifact suppression Technology Provides Reliable $S_pO_2$," *Abstracts*, A11, p. S105 (undated).

Hamilton, Patrick S., et al.; "Effect of Adaptive Motion-Artifact Reduction on QRS Detection," *Biomedical Instrumentation & Technology*, pp. 197-202 (undated).

Kim, J.M., et al.; "Signal Processing Using Fourier & Wavelet Transform," pp. II-310-II-311 (undated).

Lee, C.M., et al.; "Reduction of Motion Artifacts from Photoplethysmographic Records Using a Wavelet Denoising Approach," IEEE, pp. 194-195 (undated).

Nogawa, Masamichi, et al.; "A New Hybrid Reflectance Optical Pulse Oximetry Sensor for Lower Oxygen Saturation Measurement and for Broader Clinical Application," SPIE, vol. 2976, pp. 78-87 (undated).

Odagiri, Y.; "Pulse Wave Measuring Device," *Micromechatronics*, vol. 42, No. 3, pp. 6-11 (undated) (Article in Japanese —contains English summary of article).

Yamazaki, Nakaji, et al.; "Motion Artifact Resistant Pulse Oximeter (Durapulse PA 2100)," *Journal of Oral Cavity Medicine*, vol. 69, No. 4, pp. 53 (date unknown) (Article in Japanese —contains English summary of article).

Rheineck-Leyssius, Aart t., et al.; "Advanced Pulse Oximeter Signal Processing Technology Compared to Simple Averaging: I. Effect on Frequency of Alarms in the Operating Room," *Journal of clinical Anestesia*, vol. 11, pp. 192-195 (1990).

Azhar, N., et al.; "Automatic Feedback Control of Oxygen Therapy Using Pulse Oximetry," *Annual International Conference of the IEEE Engineering in Medicine and Biology Society*, vol. 13, No. 4, pp. 1614-1615 (1991).

Aoyagi, T., et al.; "Analysis of Motion Artifacts in Pulse Oximetry," *Japanese Society ME*, vol. 42, p. 20 (1993) (Article in Japanese—contains English summary of article).

Barreto, A.B., et al.; "Adaptive Cancelation of Motion artifact in Photoplethysmographic Blood Volume Pulse Measurements for Exercise Evaluation," *IEEE-EMBC and CMBEC—Theme 4: Signal Processing*, pp. 983-984 (1995).

Vincente, L.M., et al.; "Adaptive Pre-Processing of Photoplethysmographic Blood Volume Pulse Measurements," pp. 114-117 (1996).

Plummer, John L., et al.; "Identification of Movement Artifact by the Nellcor N-200 and N-3000 Pulse Oximeters," *Journal of clinical Monitoring*, vol. 13, pp. 109-113 (1997).

Barnum, P.T., et al.; "Novel Pulse Oximetry Technology Capable of Reliable Bradycardia Monitoring in the Neonate," *Respiratory Care*, vol. 42, No. 1, p. 1072 (Nov. 1997).

Poets, C. F., et al.; "Detection of movement artifact in recorded pulse oximeter saturation," *Eur. J. Pediatr.*; vol. 156, pp. 808-811 (1997).

Masin, Donald I., et al.; "Fetal Transmission Pulse Oximetry," *Proceedings 19th International Conference IEEE/EMBS*, Oct. 30-Nov. 2, 1997; pp. 2326-2329.

Block, Frank E., Jr., et al.; "Technology evaluation report: Obtaining pulse oximeter signals when the usual probe cannot be used," *International journal of clinical Monitoring and Computing*, vol. 14, pp. 23-28 (1997).

Nijland, Roel, et al.; "Validation of Reflectance Pulse Oximetry: An Evaluation of a new Sensor in Piglets," *Journal of Clinical Monitoring*, vol. 13, pp. 43-49 (1997).

Soto, Denise A.; "A Comparative Study of Pulse Oximeter Measurements: Digit Versus Earlobe," Master of Science Thesis, California State University Dominguez Hills, May 1997,46 pgs.

Faisst, Karin, et al.; "Intrapartum Reflectance Pulse Oximetry: Effects of Sensor Location and Fixation Duration on Oxygen Saturation Readings," *Journal of Clinical Monitoring*, vol. 13, pp. 299-302 (1997).

Izumi, Akio, et al.; "Accuracy and Utility of a New Reflectance Pulse Oximeter for Fetal Monitoring During Labor," *Journal of Clinical Monitoring*, vol. 13, pp. 103-108 (1997).

Mannheimer, Paul D., et al.; "Wavelength Selection for Low-Saturation Pulse Oximetry," *IEEE Transactions on Biomedical Engineering*, vol. 44, No. 3, pp. 148-158 (Mar. 1997).

"Smaller Product, Tighter Tolerances Pose Dispensing Challenges for Medical Device Manufacturer," *Adhesives Age*, pp. 40-41 (Oct. 1997).

Buschman, J.P., et al.; "Principles and Problems of Calibration of Fetal Oximeters," *Biomedizinische Technik*, vol. 42, pp. 265-266 (1997).

Pickett, John, et al.; "Pulse Oximetry and PPG Measurements in Plastic Surgery," *Proceedings—19th International Conference—IEEE/EMBS*, Chicago, Illinois, Oct. 30-Nov. 2, 1997, pp. 2330-2332.

Leahy, Martin J., et al.; "Sensor Validation in Biomedical Applications," *IFAC Modelling and Control in Biomedical Systems*, Warwick, UK; pp. 221-226(1997).

Barreto, Armando B., et al.; "Adaptive LMS Delay Measurement in dual Blood Volume Pulse Signals for Non-Invasive Monitoring," *IEEE*, pp. 117-120 (1997).

Crilly, Paul B., et al.; "An Integrated Pulse Oximeter System for Telemedicine Applications," *IEEE Instrumentation and Measurement Technology Conference*, Ottawa, Canada; May 19-21, 1997; pp. 102-104.

Dekock, Marc; "Pulse Oximetry Probe Adhesive Disks: a Potential for Infant Aspiration," *Anesthesiology*, vol. 89, pp. 1603-1604 (1998).

East, Christine E., et al.; "Fetal Oxygen Saturation and Uterine Contractions During Labor," *American Journal of Perinatology*, vol. 15, No. 6, pp. 345-349 (Jun. 1998).

Rhee, Sokwoo, et al.; "The Ring Sensor: a New Ambulatory Wearable Sensor for Twenty-Four Hour Patient Monitoring," *Proceedings of the 20th annual International Conference of the IEEE Engineering in Medicine and Biology Society*, vol. 20, No. 4, pp. 1906-1909 (Oct. 1998).

Yang, Boo-Ho, et al.; "A Twenty-Four Hour Tele-Nursing System Using a Ring Sensor," *Proceedings of the 1998 IEEE International Conference on Robotics & Automation*, Leaven, Belgium, May 1998; pp. 387-392.

König, Volker, et al.; "Reflectance Pulse Oximetry—Principles and Obstetric Application in the Zurich System," *Journal of Clinical Monitoring and Computing*, vol. 14, pp. 403-412 (1998).

Nogawa, Masamichi, et al.; "A Novel Hybrid Reflectance Pulse Oximater Sensor with improved Linearity and General Applicability to Various Portions of the Body," *Proceedings of the 20th Annual International Conference of the IEEE Engineering in Medicine and Biology Society*, vol. 20, No. 4, pp. 1858-1861 (1998).

Hayes, Matthew J., et al.; "Quantitative evaluation of photoplethysmographic artifact reduction for pulse oximetry," *SPIE*, vol. 3570, pp. 138-147 (Sep. 1998).

Edrich, Thomas, et al.; "Can the Blood Content of the Tissues be Determined Optically During Pulse Oximetry Without Knowledge of the Oxygen Saturation?—An In-Vitro Investigation," *Proceedings of the 20th Annual International conference of the IEEE Engineering in Medicine and Biology Society*, vol. 20, No. 6, pp. 3072-3075 (1998).

Hayes, Matthew J., et al.; "Artifact reduction in photoplethysmography," *Applied Optics*, vol. 37, No. 31, pp. 7437-7446 (Nov. 1998).

Such, Hans Olaf; "Optoelectronic Non-invasive Vascular Diagnostics Using multiple Wavelength and Imaging Approach," *Dissertation*, (1998).

Lutter, N., et al.; "Comparison of Different Evaluation Methods for a Multi-wavelength Pulse Oximeter," *Biomedizinische Technik*, vol. 43, (1998).

Ferrell, T.L., et al.; "Medical Telesensors," *SPIE*, vol. 3253, pp. 193-198 (1998).

Todd, Bryan, et al.; "The Identification of Peaks in Physiological Signals," *Computers and Biomedical Research*, vol. 32, pp. 322-335 (1999).

Rhee, Sokwoo, et al.; "Design of a Artifact-Free Wearable Plethysmographic Sensor," *Proceedings of the First joint BMES/EMBS Conference*, Oct. 13-16, 1999, Altanta, Georgia, p. 786.

Rohling, Roman, et al.; "Clinical Investigation of a New Combined Pulse Oximetry and Carbon Dioxide Tension Sensor in Adult Anaesthesia," *Journal o Clinical Monitoring and Computing*, vol. 15; pp. 23-27 (1999).

Ikeda, Kenji, et al.; "Improvement of Photo-Electric Plethysmograph Applying Newly Developed Opto-Electronic Devices," *IEEE Tencon*, pp. 1109-1112 (1999).

Kaestle, S.; "An Algorithm for Reliable Processing of Pulse Oximetry Signals Under strong Noise Conditions," *Dissertation Book*, Lubeck University, Germany (1999).

Seelbach-Göbel, Birgit, et al.; "The prediction of fetal acidosis by means of intrapartum fetal pulse oximetry," *Am. J. Obstet. Gynecol.*, vol. 180, No. 1, Part 1, pp. 73-81 (1999).

Yang, Boo-Ho, et al.; "Development of the ring sensor for healthcare automation," *Robotics and Autonomous Systems*, vol. 30, pp. 273-281 (2000).

Rhee, Sokwoo, et al.; "Artifact-Resistant, Power-Efficient Design of Finger-Ring Plethysmographic Sensor—Part I: Design and Analysis," *Proceedings of the 22nd Annual EMBS International Conference*, Chicago, Illinois; Jul. 23-28, 2000; pp. 2792-2795.

Rhee, Sokwoo, et al.; "Artifact-Resistant, Power-Efficient Design of Finger-Ring Plethysmographic Sensor—Part II: Prototyping and Benchmarking," *Proceedings of the 22nd Annual EMBS International Conference*, Chicago, Illinois; Jul. 23-28, 2000; pp. 2796-2799.

Vicenzi, Martin N.; "Transesophageal versus surface pulse oximetry in intensive care unit patients," *Crit. Care Med.*; vol. 28, No. 7, pp. 2268-2270 (2000).

Goldman, Julian M.; "Masimo Signal Extraction Pulse Oximetry," *Journal of Clinical Monitoring and Computing*, vol. 16, pp. 475-483 (2000).

Coetzee, Frans M.; "Noise-Resistant Pulse Oximetry Using a Synthetic Reference Signal," *IEEE Transactions on Biomedical Engineering*, vol. 47, No. 8, Aug. 2000, pp. 1018-1026.

Nilsson, Lena, et al.; "Monitoring of Respiratory Rate in Postoperative Care Using a New Photoplethysmographic Technique," *Journal of Clinical Monitoring and Computing*, vol. 16, pp. 309-315 (2000).

Nijland, Mark J.M., et al.; "Assessment of fetal scalp oxygen saturation determination in the sheep by transmission pulse oximetry," *Am. J. Obstet Gynecol.*, vol. 183, No. 6, pp. 1549-1553 (Dec. 2000).

Edrich, Thomas, et al.; "Pulse Oximetry: An Improved in Vitro Model that Reduces Blood Flow-Related Artifacts," *IEEE Transactions on Biomedical Engineering*, vol. 47, No. 3, pp. 338-343 (Mar. 2000).

Schulz, Christian Eric; "Design of a Pulse Oximetry Sensor Housing Assembly," California State University Master's Thesis, *UMI Dissertation Services*, UMI No. 1401306, (May 2000) 63 pages.

Yao, Jianchu, et al.; "Design of a Plug-and-Play Pulse Oximeter," *Proceedings of the Second Joint EMBS/BMES Conference*, Houston, Texas, Oct. 23-26, 2002; pp. 1752-1753.

Aoyagi, T., et al.; "Pulse Oximeters: background, present and future," *Neonatal Care*, vol. 13, No. 7, pp. 21-27 (2000) (Article in Japanese—contains English summary of article).

Yokota, Nakaura, Takahashi, et al.; "Pilot Model of a Reflectance-Type Pulse Oximeter for Pre-hospital Evaluation," *Journal of the Japanese Society of Emergency Medicine*, Kanto Region, vol. 21, pp. 26-27 (2000) (Article in Japanese—contains English summary of article).

Kaestle, S.; "Determining Artefact Sensitivity of New Pulse Oximeters in Laboratory Using Signals Obtained from Patient," *Biomedizinische Technik*, vol. 45 (2000).

Cubeddu, Rinaldo, et al.; "Portable 8-channel time-resolved optical imager for functional studies of biological tissues," *Photon Migration, Optical Coherence Tomography, and Microscopy, Proceedings of SPIE*, vol. 4431, pp. 260-265 (2001).

Gisiger, P.A., et al.; "OxiCarbo®, a single sensor for the non-invasive measurement of arterial oxygen saturation and $CO_2$ partial pressure at the ear lobe," *Sensor and Actuators*, vol. B-76, pp. 527-530 (2001).

Cysewska-Sobusaik, Anna; "Metrological Problems With noninvasive Transillumination of Living Tissues," *Proceedings of SPIE*, vol. 4515, pp. 15-24 (2001).

Rhee, Sokwoo, et al.; "Artifact-Resistant, Power-Efficient Design of Finger-Ring Plethysmographic Sensor," *IEEE Transactions on Biomedical Engineering*, vol. 48, No. 7, pp. 795-805 (Jul. 2001).

Belal, Suliman Yousef, et al.; "A fuzzy system for detecting distorted plethysmogram pulses in neonates and paediatric patients," *Physiol. Meas.*, vol. 22, pp. 397-412 (2001).

Hayes, Matthew J., et al.; "A New Method for Pulse Oximetry Possessing Inherent Insensitivity to Artifact," *IEEE Transactions on Biomedical Engineering*, vol. 48, No. 4, pp. 452-461 (Apr. 2001).

Gosney, S., et al.; "An alternative position for the pulse oximeter probe," *Anaesthesia*, vol. 56, p. 493 (2001).

Lopez-Sliva, Sonnia Maria Lopez, et al.; "NIR transmittance pulse oximetry system with laser diodes," *Clinical Diagnostic Systems, Proceedings of SPIE*, vol. 4255, pp. 80-87 (2001).

Maletras, Francois-Xavier, et al.; "Construction and calibration of a new design of Fiber Optic Respiratory Plethysmograph (FORP)," *Optomechanical Design and Engineering, Proceedings of SPIE*, vol. 4444, pp. 285-293 (2001).

Earthrowl-Gould, T., et al.; "Chest and abdominal surface motion measurement for continuous monitoring of respiratory function," *Proc. Instn Mech Engrs*, V215, Part H; pp. 515-520 (2001).

Gehring, Harmut, et al.; "The Effects of Motion Artifact and Low Perfusion on the Performance of a New Generation of Pulse Oximeters in Volunteers Undergoing Hypoxemia," *Respiratory Care*, Vo. 47, No. 1, pp. 48-60 (Jan. 2002).

Jopling, Michae W., et al.; "Issues in the Laboratory Evaluation of Pulse Oximeter Performance," *Anesth Analg*, vol. 94, pp. S62-S68 (2002).

Gostt, R., et al.; "Pulse Oximetry Artifact Recognition Algorithm for Computerized Anaesthetic Records," *Journal of Clinical Monitoring and Computing Abstracts*, p. 471 (2002).

Chan, K.W., et al.; "17.3: Adaptive Reduction of Motion Artifact from Photoplethysmographic Recordings using a Variable Step-Size LMS Filter," *IEEE*, pp. 1343-1346 (2002).

Relente, A.R., et al.; "Characterization and Adaptive Filtering of Motion Artifacts in Pulse Oximetry using Accelerometers," *Proceedings of the Second joint EMBS/BMES Conference*, Houston, Texas, Oct. 23-26, 2002; pp. 1769-1770.

Yamaya, Yoshiki, et al.; "Validity of pulse oximetry during maximal exercise in normoxia, hypoxia, and hyperoxia," *J. Appl. Physiol.*, vol. 92, pp. 162-168 (2002).

Lutter, Norbert O., et al.; "False Alarm Rates of Three Third-Generation Pulse Oximeters in PACU, ICU and IABP Patients," *Anesth Analg*, vol. 94, pp. S69-S75 (2002).

Lutter, N., et al.; "Accuracy of Noninvasive Continuous Blood Pressure; Measurement Utilising the Pulse Transit Time," *Journal of clinical Monitoring and Computing*, vol. 17, Nos. 7-8, pp. 469 (2002).

Liu, Ying, et al.; "Sensor design of new type reflectance pulse oximetry," *Optics in Health Care and Biomedical Optics: Diagnostics and Treatment, Proceedings of SPIE*, vol. 4916, pp. 98-102 (2002).

Kyriacou, Panayiotis A., et al.; "Esophageal Pulse Oximetry Utilizing Reflectance Photoplethysmography," *IEEE Transactions on Biomedical Engineering*, vol. 49, No. 11, pp. 1360-1368 (Nov. 2002).

Kyriacou, P. A., et al.; "Investigation of oesophageal photoplethysmographic signals and blood oxygen saturation measurements in cardiothoracic surgery patients," *Physiological Measurement*, vol. 23, No. 3, pp. 533-545 (Aug. 2002).

Tobata, H., et al.; "Study of Ambient Light Affecting Pulse Oximeter Probes," *Ikigaku (Medical Technology)*, vol. 71, No. 10, pp. 475-476 (2002) (Article in Japanese—contains English summary of article).

Irie, A., et al.; "Respiration Monitors—Pulse Oximeters," *Neonatal Care*, vol. 15, No. 12, pp. 78-83 (2002) (Article in Japanese—contains English summary of article).

Koga, I., et al.; "Sigmoid colonic reflectance pulse oximetry and tonometry in a porcine experimental hypoperfusion shock model," *Acta Anaesthesiol Scand*, vol. 46, pp. 1212-1216 (2002).

Shaltis, Phillip, et al.; "Implementation and Validation of a Power-Efficient, High-Speed Modulation Design for Wireless Oxygen Saturation Measurement Systems," *IEEE*, pp. 193-194 (2002).

Warren, Steve, et al.; "Wearable Sensors and Component-Based Design for Home Health Care," *Proceedings of the Second Joint EMBS/BMES Conference*, Houston, Texas; Oct. 23-26, 2002; pp. 1871-1872.

Ericson, M.N., et al.; "In vivo application of a minimally invasive oximetry based perfusion sensor," *Proceedings of the Second Joint EMBS/BMES Conference*, Houston, Texas; Oct. 23-26, 2002, pp. 1789-1790.

Yoon, Gilwon, et al.; "Multiple diagnosis based on Photoplethysmography: hematocrib, SpO2, pulse and respiration," *Optics in Health Care and Biomedical optics: Diagnostics and Treatment; Proceedings of the SPIE*, vol. 4916; pp. 185-188 (2002).

Hase, Kentaro, et al.; "Continuous Measurement of Blood Oxygen Pressure Using a Fiber Optic Sensor Based on Phosphorescense Quenching," *Proceedings of the Second Joint EMBS/BMES Conference*, Houston, Texas; Oct. 23-26, 2002, pp. 1777-1778.

Pothisarn, W., et al.; "A non-invasive hemoglobin measurement based pulse oximetry," *Optics in Health Care and Biomedical Optics: Diagnostics and Treatment; Proceedings of SPIE*, vol. 4916; pp. 498-504 (2002).

Tremper, K.K.; "A Second Generation Technique for Evaluating Accuracy and Reliability of Second Generation Pulse Oximeters," *Journal of Clinical Monitoring and Computing*, vol. 16, pp. 473-474 (2001).

Lopez-Sliva, Sonnia Maria Lopez, et al.; "Near-infrared transmittance pulse oximetry with laser diodes," *Journal of Biomedical Optics*, vol. 8, No. 3, pp. 525-533 (Jul. 2003).

Cyrill, D., et al.; "Adaptive Comb Filter for Quasi-Periodic Physiologic Signals," *Proceedings of the 25th Annual International Conference of the IEEE EMBS*, Cancun, Mexico, Sep. 17-21, 2003; pp. 2439-2442.

Matthews, Nora S. et al.; "An evaluation of pulse oximeters in dogs, cats and horses," *Veterinary Anaesthesia and Analgesia*, vol. 30, pp. 3-14 (2003).

Stetson, Paul F.; "Determining Heart Rate from Noisey Pulse Oximeter Signals Using Fuzzy Logic," *The IEEE International Conference on Fuzzy Systems*, St. Louis, Missouri, May 25-28, 2003; pp. 1053-1058.

Aoyagi, Takuo; "Pulse oximetry: its invention, theory, and future," *Journal of Anesthesia*, vol. 17, pp. 259-266 (2003).

Avidan, A.; "Pulse oximeter ear probe," *Anaesthesia*, vol. 58, pp. 726 (2003).

Mendelson, Y., et al.; "Measurement Site and Photodetector Size Considerations in Optimizing Power Consumption of a Wearable Reflectance Pulse Oximeter," *Proceedings of the 25th Annual International conference of the IEEE EMBS*, Cancun, Mexico, Sep. 17-21, 2003; pp. 3016-3019.

Itoh, K., et al.; "Pulse Oximeter," *Toyaku Zasshi* (Toyaku Journal), vol. 25, No. 8, pp. 50-54 (2003) (Article in Japanese—contains English summary of article).

Matsui, A., et al.; "Pulse Oximeter," *Neonatal Care*, vol. 16, No. 3, pp. 38-45 (2003) (Article in Japanese—contains English summary of article).

Nakagawa, M., et al.; "Oxygen Saturation Monitor," *Neonatal Monitoring*, vol. 26, No. 5, pp. 536-539 (2003) (Article in Japanese—contains English summary of article).

Kubota, H., et al.; "Simultaneous Monitoring of PtcCO2 and Sp02 using a Miniature earlobe sensor," *Jinko Kokyo* (*Aritificial Respiration*), vol. 20, No. 1, pp. 24-29 (2003).

Lebak, J.W., et al.; "Implementation of a Standards-Based Pulse Oximeter on a Wearable, Embedded Platform," *Proceeding of the 25th Annual International Conference of the IEEE EMBS*, Cancun, Mexico, Sep. 17-21, 2003; pp. 3196-3198.

Nagl, L., et al.; "Wearable Sensor System for Wireless State-of-Health Determination in Cattle," *Proceeding of the 25th Annual International Conference of the IEEE EMBS*, Cancun, Mexico, Sep. 17-21, 2003; pp. 3012-3015.

Östmark, Åke, et al.; "Mobile Medical Applications Made Feasible Through Use of EIS Platforms," *IMTC—Instrumentation and Measurement Technology Conference*, Vail, Colorado; May 20-22, 2003; pp. 292-295.

Warren, Steve, et al.; "A Distributed Infrastructure for Veterinary Telemedicine," *Proceedings of the 25th Annual International Conference of the IEEE EMBS*, Cancun, Mexico; Sep. 17-21, 2003; pp. 1394-1397.

Pujary, C., et al.; "Photodetector Size Considerations in the Design of a Noninvasive Reflectance Pulse Oximeter for Telemedicine Applications," *IEEE*, pp. 148-149 (2003).

Johansson; A. "Neural network for photoplethysmographic respiratory rate monitoring," *Medical & Biological Engineering & Computing*, vol. 41, pp. 242-248 (2003).

Reuss, James L.; "Factors Influencing Fetal Pulse Oximetry Performance," *Journal of clinical Monitoring and Computing*, vol. 18, pp. 13-14 (2004).

Mannheimer, Paul D., et al.; "The influence of Larger Subcutaneous Blood Vessels on Pulse Oximetry," *Journal of clinical Monitoring and Computing*, vol. 18, pp. 179-188 (2004).

Wendelken, Suzanne, et al.; "The Feasibility of Using a Forehead Reflectance Pulse Oximeter for Automated Remote Triage," *IEEE*, pp. 180-181(2004).

Lopez-Silva, S.M., et al.; "Transmittance Photoplethysmography and Pulse Oximetry With Near Infrared Laser Diodes," *IMTC 2004—Instrumentation and Measurement Technology Conference*, Como, Italy, May 18-20, 2004; pp. 718-723.

Sugino, Shigekzau, et al.; "Forehead is as sensitive as finger pulse oximetry during general anesthesia," *Can J. Anesth.; General Anesthesia*, vol. 51, No. 5; pp. 432-436 (2004).

Addison, Paul S., et al.; "A novel time-frequency-based 3D Lissajous figure method and its application to the determination of oxygen saturation from the photoplethysmogram," *Institute of Physic Publishing, Meas. Sci. Technol.*, vol. 15, pp. L15-L18 (2004).

Jovanov, E., et al.; "Reconfigurable intelligent Sensors for Health Monitoring: A case Study of Pulse Oximeter Sensor," *Proceedings o the 26th Annual International conference of the IEEE EMBS*, San Francisco, California, Sep. 1-5, 2004, pp. 4759-4762.

Kocher, Serge, et al.; "Performance of a Digital $PCO_2/SPO_2$ Ear Sensor," *Journal of Clinical Monitoring and Computing*, vol. 18, pp. 75-59 (2004).

Yao, Jianchu, et al.; "A Novel Algorithm to Separate Motion Artifacts from Photoplethysmographic Signals Obtained With a Reflectance Pulse Oximeter," *Proceedings of the 26th Annual International conference of the IEEE EMBS*, San Francisco, California, Sep. 1-5, 2004; pp. 2153-2156.

Nuhr, M., et al.: "Forehead $SpO_2$ monitoring compared to finger $SpO_2$ recording in emergency transport," *Anaesthesia*, vol. 59, pp. 390-393 (2004).

Johnston, William S., et al.; "Effects of Motion Artifacts on helmet-Mounted Pulse Oximeter Sensors," 2 pgs. (2004).

Branche, Paul C., et al.; "Measurement Reproducibility and Sensor Placement Considerations in Designing a Wearable Pulse Oximeter for Military Applications," 2 pgs. (2004).

Heuss, Ludwig T., et al.; "Combined Pulse Oximetry / Cutaneous Carbon dioxide Tension Monitoring During Colonoscopies: Pilot study with a Smart Ear Clip," *Digestion*, vol. 70, pp. 152-158 (2004).

Matsuzawa, Y., et al.; "Pulse Oximeter," *Home Care Medicine*, pp. 42-45 (Jul. 2004); (Article in Japanese—contains English summary of article).

Crespi, F., et al.; "Near infrared oxymeter prototype for non-invasive analysis of rat brain oxygenation," *Optical Sensing, Proceedings of SPIE*, vol. 5459, pp. 38-45 (2004).

Johnston, W.S., et al.; "Extracting Breathing Rate Infromation from a Wearable Reflectance Pulse Oximeter Sensor," *Proceedings of the 26th Annual International conference of the IEEE EMBS*, San Francisco, California; Sep. 1-5, 2004; pp. 5388-5391.

Spigulis, Janis, et al.; "Optical multi-channel sensing of skin blood pulsations," *Optical Sensing, Proceedings of SPIE*, vol. 5459, pp. 46-53 (2004).

Yan, Yong-sheng, et al.; "Reduction of motion artifact in pulse oximetry by smoothed pseudo Wigner-Ville distribution," *Journal of NeuroEngineering and Rehabilitation*, vol. 2, No. 3 (9 pages) (Mar. 2005).

Urquhart, C., et al.; "Ear probe pulse oximeters and neonates," *Anaesthesia*, vol. 60, p. 294 (2005).

Jonnson, P.O. "Patent Cooperation Treaty PCT Written Opinion of the International Searching Authority"; Apr. 20, 2007; 12pp.; European Patent Office; Berlin.

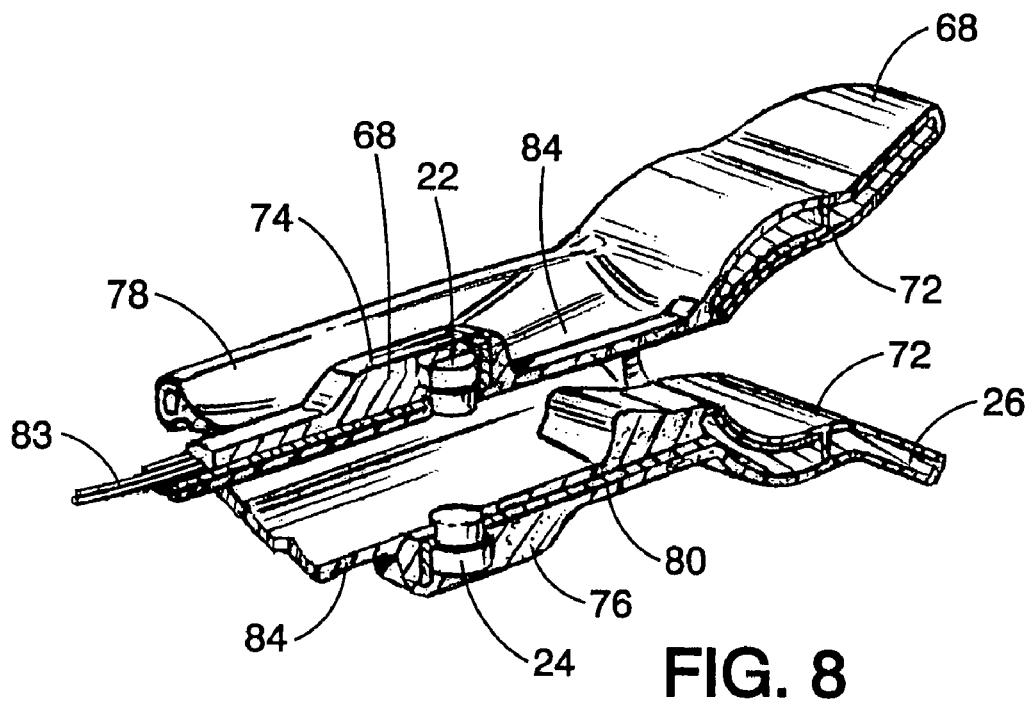
FIG. 8
FIG. 9
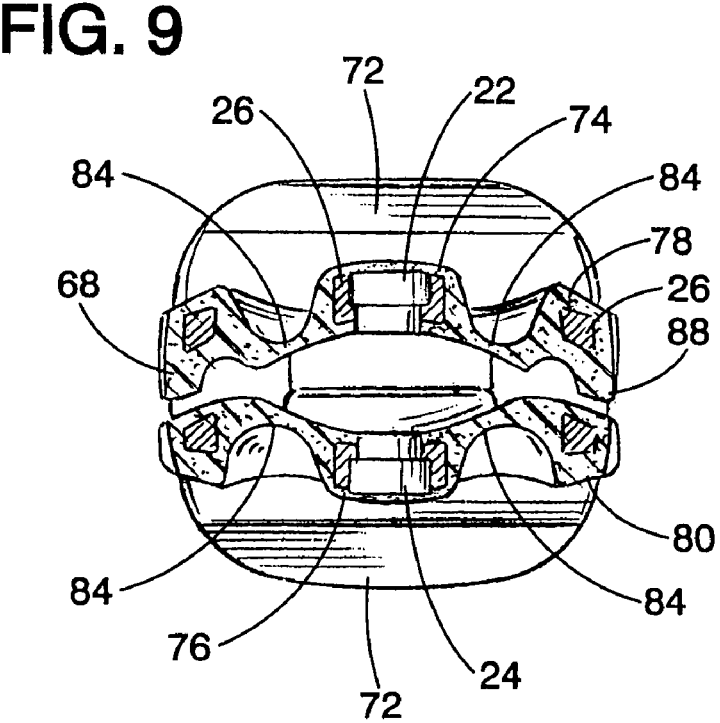

MEDICAL SENSOR AND TECHNIQUE FOR USING THE SAME

CROSS-REFERENCE TO RELATED APPLICATION

This application is a continuation of U.S. application Ser. No. 11/199,524 filed Aug. 8, 2005, the disclosure of which is hereby incorporated by reference in its entirety.

BACKGROUND OF THE INVENTION

1. Field of the Invention

The present invention relates generally to medical devices and, more particularly, to sensors used for sensing physiological parameters of a patient.

2. Description of the Related Art

This section is intended to introduce the reader to various aspects of art that may be related to various aspects of the present invention, which are described and/or claimed below. This discussion is believed to be helpful in providing the reader with background information to facilitate a better understanding of the various aspects of the present invention. Accordingly, it should be understood that these statements are to be read in this light, and not as admissions of prior art.

In the field of medicine, doctors often desire to monitor certain physiological characteristics of their patients. Accordingly, a wide variety of devices have been developed for monitoring physiological characteristics. Such devices provide doctors and other healthcare personnel with the information they need to provide the best possible healthcare for their patients. As a result, such monitoring devices have become an indispensable part of modern medicine.

One technique for monitoring certain physiological characteristics of a patient is commonly referred to as pulse oximetry, and the devices built based upon pulse oximetry techniques are commonly referred to as pulse oximeters. Pulse oximetry may be used to measure various blood flow characteristics, such as the blood-oxygen saturation of hemoglobin in arterial blood, the volume of individual blood pulsations supplying the tissue, and/or the rate of blood pulsations corresponding to each heartbeat of a patient.

Pulse oximeters typically utilize a non-invasive sensor that is placed on or against a patient's tissue that is well perfused with blood, such as a patient's finger, toe, forehead or earlobe. The pulse oximeter sensor emits light and photoelectrically senses the absorption and/or scattering of the light after passage through the perfused tissue. The data collected by the sensor may then be used to calculate one or more of the above physiological characteristics based upon the absorption or scattering of the light. More specifically, the emitted light is typically selected to be of one or more wavelengths that are absorbed or scattered in an amount related to the presence of oxygenated versus de-oxygenated hemoglobin in the blood. The amount of light absorbed and/or scattered may then be used to estimate the amount of the oxygen in the tissue using various algorithms.

In many instances, it may be desirable to employ, for cost and/or convenience, a pulse oximeter sensor that is reusable. Such reusable sensors, however, may be uncomfortable for the patient for various reasons. For example, the materials used in their construction may not be adequately compliant or supple or the structural features may include angles or edges.

Furthermore, the reusable sensor should fit snugly enough that incidental patient motion will not dislodge or move the sensor, yet not so tight that it may interfere with pulse oximetry measurements. Such a conforming fit may be difficult to achieve over a range of patient physiologies without adjustment or excessive attention on the part of medical personnel. In addition, lack of a tight or secure fit may allow light from the environment to reach the photodetecting elements of the sensor. Such environmental light is not related to a physiological characteristic of the patient and may, therefore, introduce error into the measurements derived using data obtained with the sensor.

Reusable pulse oximeter sensors are also used repeatedly and, typically, on more than one patient. Therefore, over the life of the sensor, detritus and other bio-debris (sloughed off skin cells, dried fluids, dirt, and so forth) may accumulate on the surface of the sensor or in crevices and cavities of the sensor, after repeated uses. As a result, it may be desirable to quickly and/or routinely clean the sensor in a thorough manner. However, in sensors having a multi-part construction, as is typical in reusable pulse oximeter sensors, it may be difficult to perform such a quick and/or routine cleaning. For example, such a thorough cleaning may require disassembly of the sensor and individual cleaning of the disassembled parts or may require careful cleaning using utensils capable of reaching into cavities or crevices of the sensor. Such cleaning is labor intensive and may be impractical in a typical hospital or clinic environment.

SUMMARY

Certain aspects commensurate in scope with the originally claimed invention are set forth below. It should be understood that these aspects are presented merely to provide the reader with a brief summary of certain forms the invention might take and that these aspects are not intended to limit the scope of the invention. Indeed, the invention may encompass a variety of aspects that may not be set forth below.

There is provided a sensor assembly that includes: a frame comprising two or more structural supports; a coating provided over the frame, wherein the coating comprises at least one deformable region disposed between the two or more structural supports; at least one optical component disposed within the at least one deformable region, such that the at least one optical component can move relative to the two or more structural supports; and a biasing component attached to an end of the frame such that at least two different portions of the coated frame are biased closed in the absence of a sufficient opening force.

There is also provided a skeletal frame of a sensor that includes: two or more structural support members having one or more spaces between the two or more structural support members, wherein the two or more structural support members are configured to provide support to an overlying coating when present.

There is also provided a method for manufacturing a skeletal framework of a sensor that includes: forming two or more structural support members of a skeletal frame of a sensor having one or more spaces between the two or more structural support members, wherein the two or more structural support members are configured to provide support to an overlying coating when present.

BRIEF DESCRIPTION OF THE DRAWINGS

Advantages of the invention may become apparent upon reading the following detailed description and upon reference to the drawings in which:

FIG. 8 illustrates a cross-section taken along section line 8-8 of the overmolded patient sensor depicted in FIG. 6; and FIG. 9 illustrates a cross-section taken along section line 9-9 of the overmolded patient sensor depicted in FIG. 6.

DETAILED DESCRIPTION OF SPECIFIC EMBODIMENTS

Figure 1:
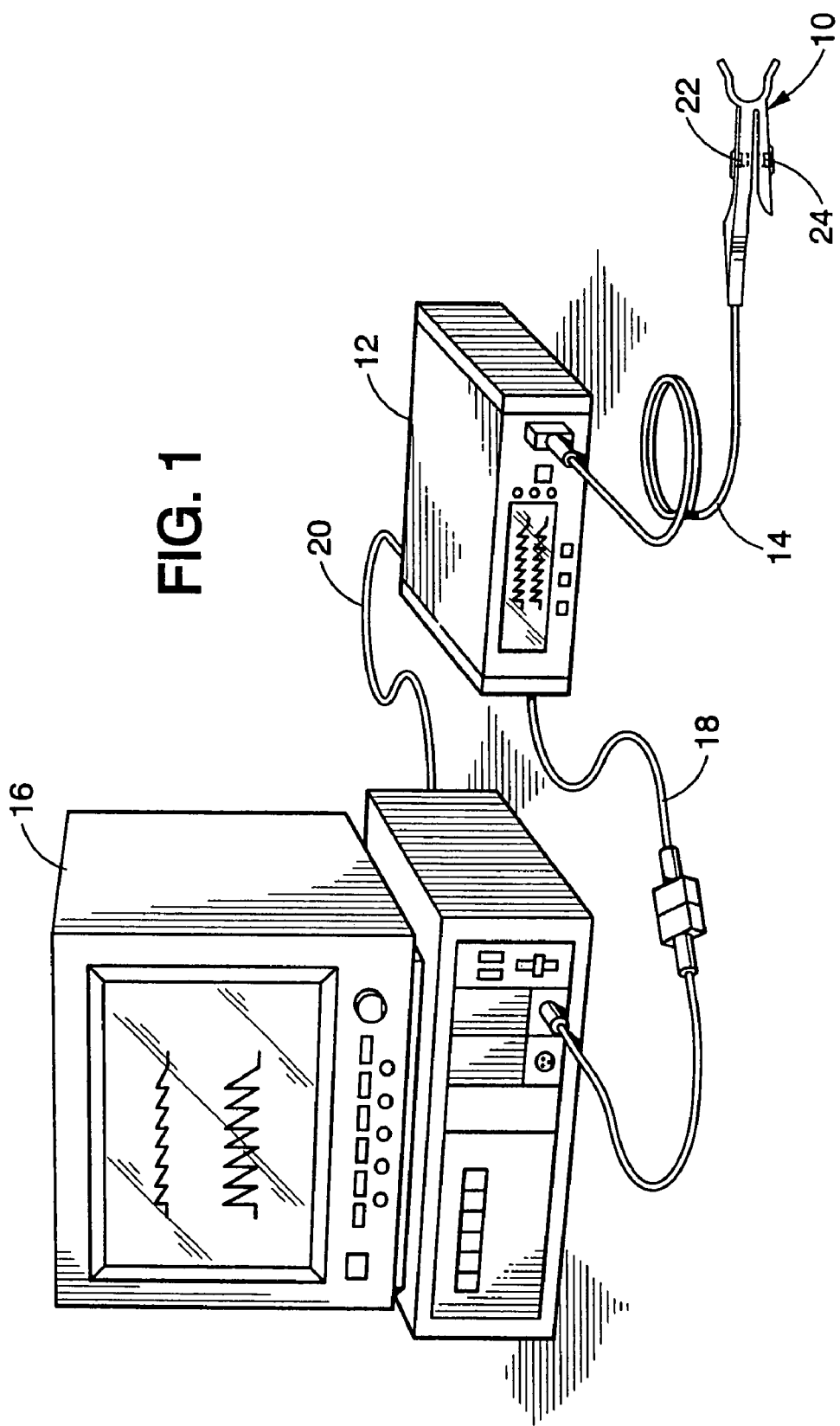
FIG. 1 illustrates a patient monitoring system coupled to a multi-parameter patient monitor and a sensor, in accordance with aspects of the present technique.

One or more specific embodiments of the present invention will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

It is desirable to provide a comfortable and conformable reusable patient sensor, such as for use in pulse oximetry or other applications utilizing spectrophotometry, that is easily cleaned and that is resistant to environmental light infiltration. In accordance with some aspects of the present technique, a reusable patient sensor is provided that is overmolded to provide patient comfort and a suitably conformable fit. The overmold material provides a seal against bodily fluids, as well as water or other cleaning fluids, that allows easy cleaning without disassembly or special tools. In accordance with some aspects of the present technique, the reusable patient sensor includes a mechanism providing a biasing force, such as a metal flat spring or a torsion spring, to facilitate the secure placement of the sensor on a patient.

Prior to discussing such exemplary sensors in detail, it should be appreciated that such sensors are typically designed for use with a patient monitoring system. For example, referring now to FIG. 1, a sensor 10 according to the present invention may be used in conjunction with a patient monitor 12. In the depicted embodiment, a cable 14 connects the sensor 10 to the patient monitor 12. As will be appreciated by those of ordinary skill in the art, the sensor 10 and/or the cable 14 may include or incorporate one or more integrated circuit devices or electrical devices, such as a memory, processor chip, or resistor, that may facilitate or enhance communication between the sensor 10 and the patient monitor 12. Likewise the cable 14 may be an adaptor cable, with or without an integrated circuit or electrical device, for facilitating communication between the sensor 10 and various types of monitors, including older or newer versions of the patient monitor 12 or other physiological monitors. In other embodiments, the sensor 10 and the patient monitor 12 may communicate via wireless means, such as using radio, infrared, or optical signals. In such embodiments, a transmission device (not shown) may be connected to the sensor 10 to facilitate wireless transmission between the sensor 10 and the patient monitor 12. As will be appreciated by those of ordinary skill in the art, the cable 14 (or corresponding wireless transmissions) are typically used to transmit control or timing signals from the monitor 12 to the sensor 10 and/or to transmit acquired data from the sensor 10 to the monitor 12. In some embodiments, however, the cable 14 may be an optical fiber that allows optical signals to be conducted between the monitor 12 and the sensor 10.

In one embodiment, the patient monitor 12 may be a suitable pulse oximeter, such as those available from Nellcor Puritan Bennett Inc. In other embodiments, the patient monitor 12 may be a monitor suitable for measuring tissue water fractions, or other body fluid related metrics, using spectrophotometric or other techniques. Furthermore, the monitor 12 may be a multi-purpose monitor suitable for performing pulse oximetry and measurement of tissue water fraction, or other combinations of physiological and/or biochemical monitoring processes, using data acquired via the sensor 10. Furthermore, to upgrade conventional monitoring functions provided by the monitor 12 to provide additional functions, the patient monitor 12 may be coupled to a multi-parameter patient monitor 16 via a cable 18 connected to a sensor input port and/or via a cable 20 connected to a digital communication port.

The sensor 10, in the example depicted in FIG. 1, is a clip-style sensor that is overmolded to provide a unitary or enclosed assembly. The sensor 10 includes an emitter 22 and a detector 24 which may be of any suitable type. For example, the emitter 22 may be one or more light emitting diodes adapted to transmit one or more wavelengths of light, such as in the red to infrared range, and the detector 24 may be a photodetector, such as a silicon photodiode package, selected to receive light in the range emitted from the emitter 22. In the depicted embodiment, the sensor 10 is coupled to a cable 14 that is responsible for transmitting electrical and/or optical signals to and from the emitter 22 and detector 24 of the sensor 10. The cable 14 may be permanently coupled to the sensor 10, or it may be removably coupled to the sensor 10—the latter alternative being more useful and cost efficient in situations where the sensor 10 is disposable.

The sensor 10 described above is generally configured for use as a "transmission type" sensor for use in spectrophotometric applications, though in some embodiments it may instead be configured for use as a "reflectance type sensor." Transmission type sensors include an emitter and detector that are typically placed on opposing sides of the sensor site. If the sensor site is a fingertip, for example, the sensor 10 is positioned over the patient's fingertip such that the emitter and detector lie on either side of the patient's nail bed. For example, the sensor 10 is positioned so that the emitter is located on the patient's fingernail and the detector is located opposite the emitter on the patient's finger pad. During operation, the emitter shines one or more wavelengths of light through the patient's fingertip, or other tissue, and the light received by the detector is processed to determine various physiological characteristics of the patient.

Reflectance type sensors generally operate under the same general principles as transmittance type sensors. However, reflectance type sensors include an emitter and detector that are typically placed on the same side of the sensor site. For example, a reflectance type sensor may be placed on a patient's fingertip such that the emitter and detector are positioned side-by-side. Reflectance type sensors detect light photons that are scattered back to the detector.

For pulse oximetry applications using either transmission or reflectance type sensors the oxygen saturation of the patient's arterial blood may be determined using two or more wavelengths of light, most commonly red and near infrared wavelengths. Similarly, in other applications a tissue water fraction (or other body fluid related metric) or a concentration of one or more biochemical components in an aqueous environment may be measured using two or more wavelengths of light, most commonly near infrared wavelengths between about 1,000 nm to about 2,500 nm. It should be understood that, as used herein, the term "light" may refer to one or more of infrared, visible, ultraviolet, or even X-ray electromagnetic radiation, and may also include any wavelength within the infrared, visible, ultraviolet, or X-ray spectra.

Pulse oximetry and other spectrophotometric sensors, whether transmission-type or reflectance-type, are typically placed on a patient in a location conducive to measurement of the desired physiological parameters. For example, pulse oximetry sensors are typically placed on a patient in a location that is normally perfused with arterial blood to facilitate measurement of the desired blood characteristics, such as arterial oxygen saturation measurement ($SaO_2$). Common pulse oximetry sensor sites include a patient's fingertips, toes, forehead, or earlobes. Regardless of the placement of the sensor 10, the reliability of the pulse oximetry measurement is related to the accurate detection of transmitted light that has passed through the perfused tissue and has not been inappropriately supplemented by outside light sources or modulated by subdermal anatomic structures. Such inappropriate supplementation and/or modulation of the light transmitted by the sensor can cause variability in the resulting pulse oximetry measurements.

As noted above, the overmolded sensor 10 discussed herein may be configured for either transmission or reflectance type sensing. For simplicity, the exemplary embodiment of the sensor 10 described herein is adapted for use as a transmission-type sensor. As will be appreciated by those of ordinary skill in the art, however, such discussion is merely exemplary and is not intended to limit the scope of the present technique.

Figure 2:
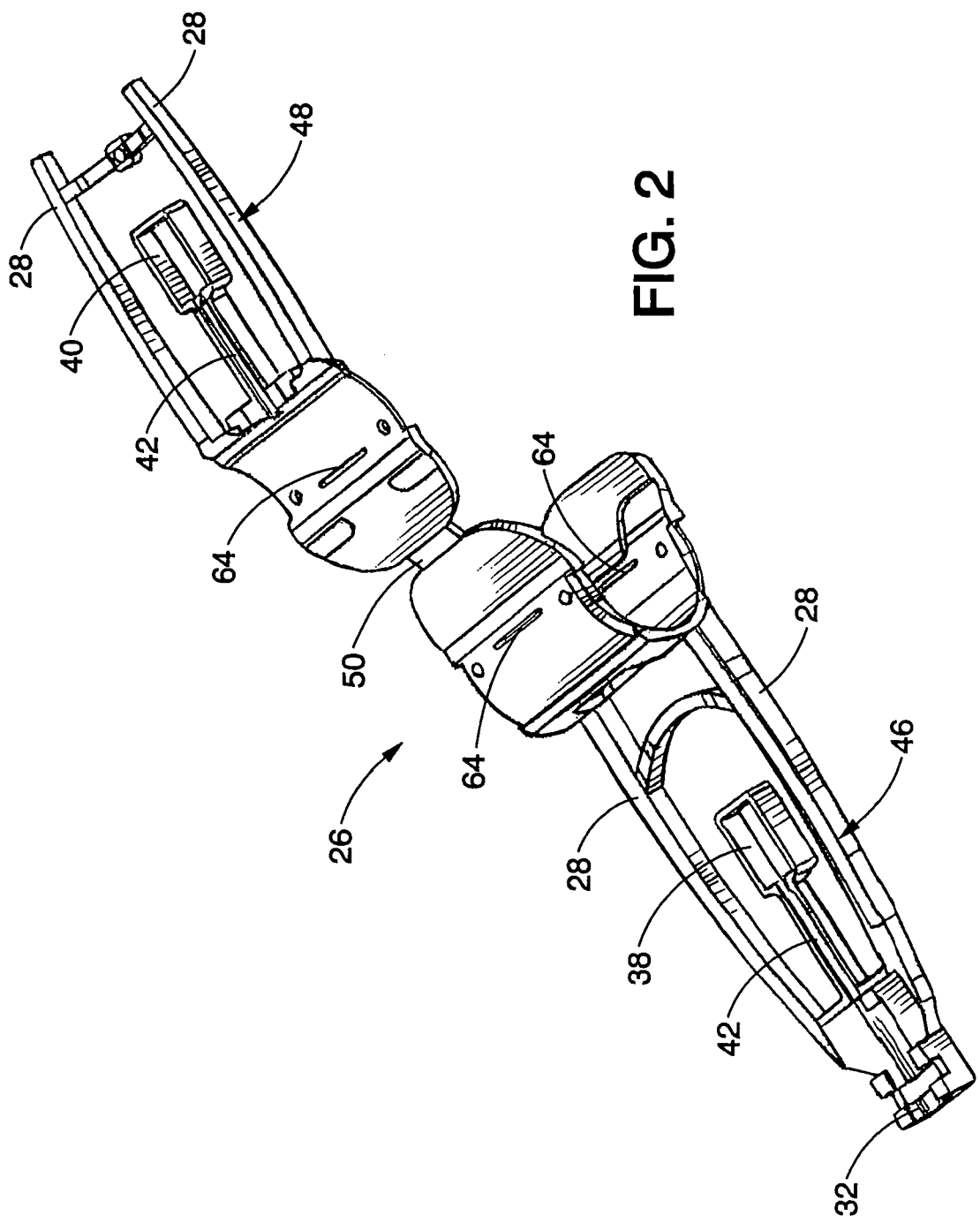
FIG. 2 illustrates a perspective view of an internal frame for use in a patient sensor, in accordance with aspects of the present technique.

Referring now to FIG. 2, an internal frame 26 for a sensor 10 is depicted. In the depicted example, the internal frame 26 is a skeletal frame for the sensor 10. Such a skeletal frame may include different structures or regions that may or may not have similar rigidities. For example, the depicted skeletal frame includes structural supports 28 that define the general shape of the sensor 10 when coated, as discussed below with regard to FIGS. 6-9. In view of their structure providing function, the structural supports 28 may be constructed to be substantially rigid or semi-rigid. In addition, the skeletal frame may include a cable guide 32 through which a cable, such as an electrical or optical cable, may pass to connect to the electrical or optical conductors attached to the emitter 22 and/or detector 24 upon assembly. Likewise, a skeletal frame, such as the depicted internal frame 26, may include component housings, such as the emitter housing 38 and detector housing 40 and struts 42 attaching such housings to the remainder of the skeletal frame. The struts 42 may be relatively flexible, allowing the emitter housing 38 and/or the detector housing 40 to move vertically (such as along an optical axis between the respective housings) relative to the structural supports 28 of the skeletal frame. Alternatively, in embodiments where the struts 42 are relatively rigid, where multiple struts 42 are employed to attach the housings 38 and 40 to the structural supports 28, or where the internal frame is substantially solid instead of skeletal, the housings 38 and/or 40 may be fixed relative to the respective structural supports 28 and, therefore, move with the structural supports 28.

Figure 3:
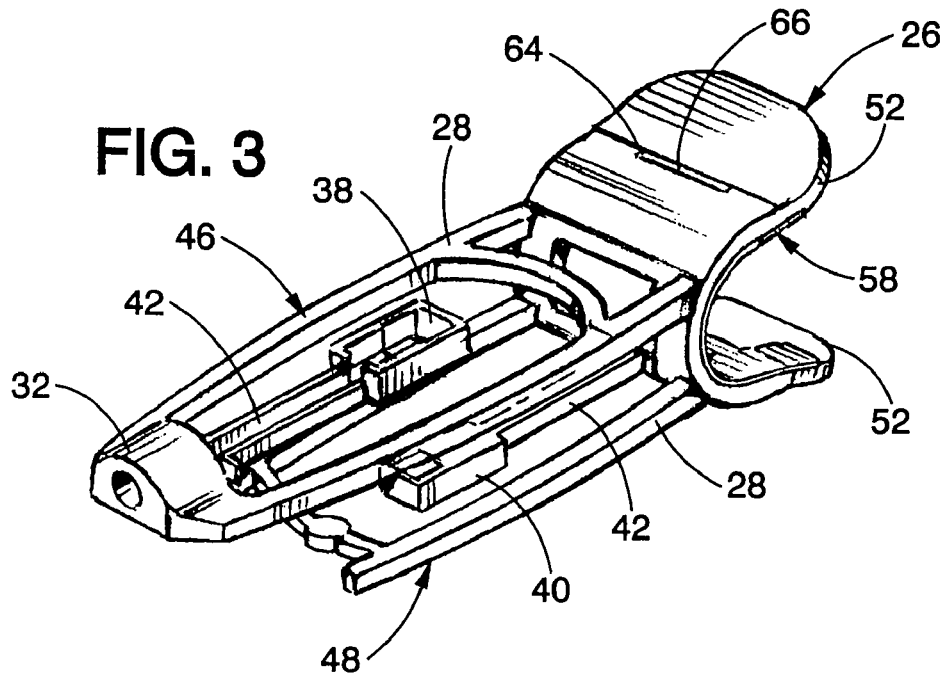
FIG. 3 illustrates a perspective view of the internal frame of FIG. 2 in a closed configuration, in accordance with aspects of the present technique.

In embodiments where the internal frame 26 is skeletal, the various structural supports 28, housings 38 and 40, struts 42, and other structures may define various openings and spaces between and/or around the structures of the skeletal frame. In this manner, the skeletal frame provides structural support at specific locations for a coating or overmolding. However, in regions where structural support is not provided, flexibility and freedom of motion in an overlying coating or overmolding may be possible. For example, in one implementation, the emitter housing 38 and/or the detector housing 40 may be attached to the remainder of the skeletal frame by flexible struts 42, as depicted in FIGS. 2-4. In such implementations, a coating provided proximate to the emitter housing 38 and/or detector housing 40 may be sufficiently flexible (such as due to the elasticity and/or the thinness of the coating material in the open areas of the skeletal frame) such that the housings 38 and 40 may move independent of the structural supports 28 of the frame 26 along an optical axis between the housings 38 and 40.

In certain embodiments, the internal frame 26 is constructed, in whole or in part, from polymeric materials, such as thermoplastics, capable of providing a suitable rigidity or semi-rigidity for the different portions of the internal frame 26. Examples of such suitable materials include polypropylene and nylon, though other polymeric materials may also be suitable. For example, in one embodiment, the internal frame 26 is constructed from polyurethane having a durometer of 65 Shore D. In other embodiments, the internal frame 26 is constructed, in whole or in part, from other suitably rigid or semi-rigid materials, such as stainless steel, aluminum, magnesium, graphite, fiberglass, or other metals, alloys, or compositions that are sufficiently ductile and/or strong. For example, metals, alloys, or compositions that are suitable for diecasting, sintering, lost wax casting, stamping and forming, and other metal or composition fabrication processes may be used to construct the internal frame 26.

In addition, the internal frame 26 may be constructed as an integral structure or as a composite structure. For example, in one embodiment, the internal frame 26 may be constructed as a single piece from a single material or from different materials. Alternatively, the internal frame 26 may be constructed or assembled from two or more parts that are separately formed. In such embodiments, the different parts may be formed from the same or different materials. For example, in implementations where different parts are formed from different materials, each part may be constructed from a material having suitable mechanical and/or chemical properties for that part. The different parts may then be joined or fitted together to form the internal frame 26.

In addition, the internal frame 26 may be molded, formed, or constructed in a different configuration than the final sensor configuration. For example, referring now to FIG. 2, the internal frame 26 for use in the sensor 10 may be initially formed in a generally open, or flat, configuration compared to the relatively closed configuration of the internal frame 26 when folded to form the sensor 10. In such embodiments, a top portion 46 and a bottom portion 48 of the frame 26 may be formed in a generally open or planar configuration in which the two portions 46 and 48 are connected by a connective portion 50.

Figure 4A:
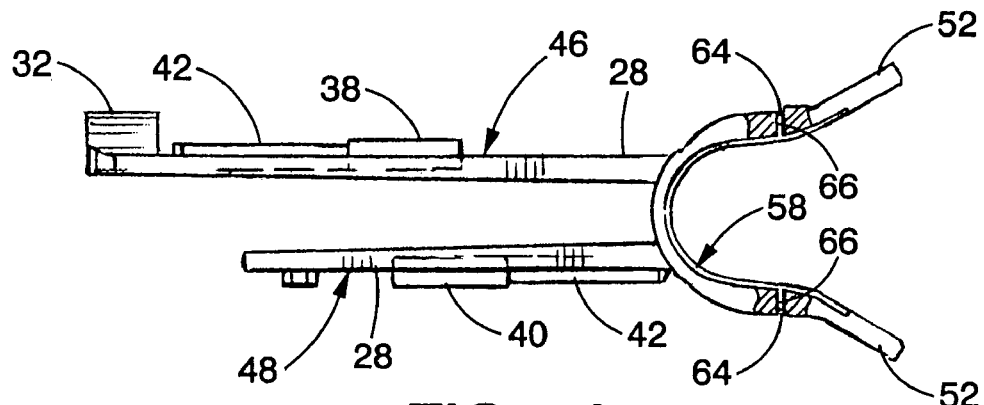
FIG. 4A illustrates a side view of the internal frame of FIG. 3.
Figure 5A:
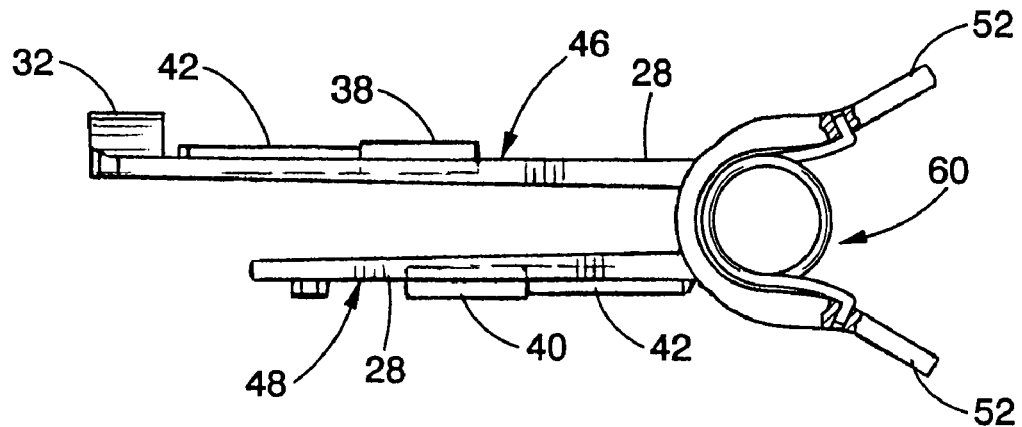
FIG. 5A illustrates a side view of another internal frame for use in a patient sensor, in accordance with aspects of the present technique.

For example, the top portion 46, bottom portion 48, and connective portion 50 may be molded or formed as a single piece in an open configuration. In such an embodiment, the connective portion 50 may be broken or deformed to bring the top portion 46 and bottom portion 48 into a closed configuration, as depicted in FIGS. 3, 4A, and 5A. In this implementation, the top portion 46 and bottom portion 48 may be secured together, such as via a snap fitting process, ultrasonic welding, or heat staking or by application of an adhesive or mechanical fastener.

Alternatively, the internal frame 26 may be formed as multiple parts that are joined together to form the internal frame 26. For example, the top portion 46, bottom portion 48, tabs 52 and/or the connective portion 50 may be molded or formed separately and subsequently secured together to form the internal frame 26. The different parts of the internal frame 26 may be joined together using one or more of the techniques noted above, such as a snap fitting process, ultrasonic welding, or heat staking or by application of an adhesive or mechanical fastener. If the internal frame 26 is secured together in an open configuration, the connective portion 50 may be broken or deformed to bring the top portion 46 and bottom portion 48 into a closed configuration, as depicted in FIGS. 3 4A, and 5A. Alternatively, the internal frame 26 may be constructed in a closed configuration from the separately molded or formed parts, such as the top portion 46, bottom portion 48, and/or tabs 52.

Figure 4B:
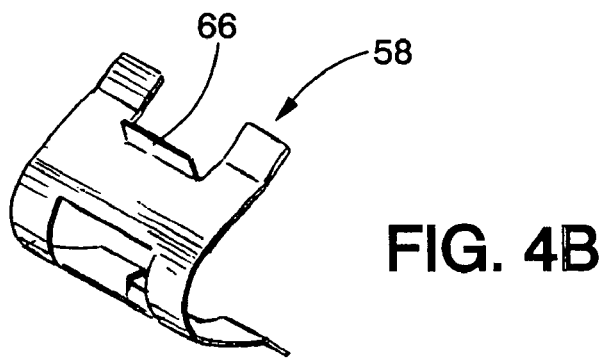
FIG. 4B illustrates a flat spring for use with the internal frame of FIGS. 2-4A, in accordance with aspects of the present technique.
Figure 5B:
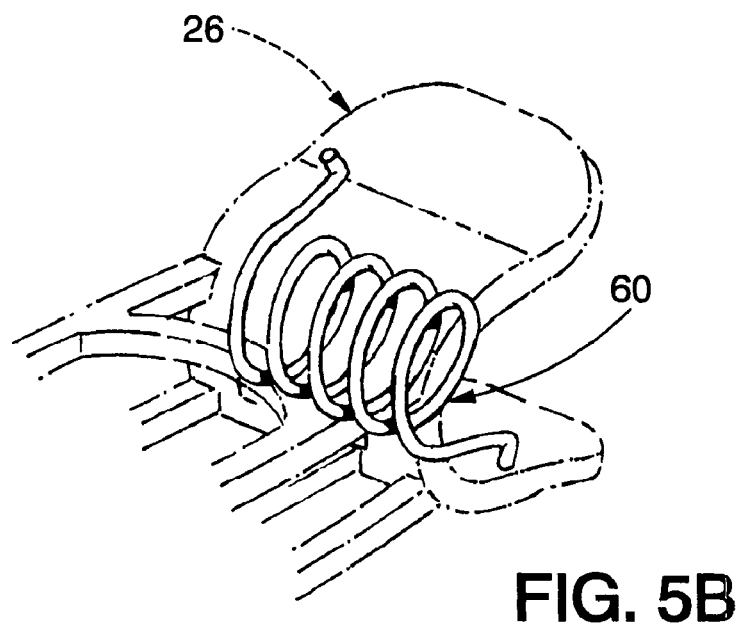
FIG. 5B illustrates a torsion spring for use with the internal frame of FIG. 5A, in accordance with aspects of the present technique.

In certain embodiments, the internal frame 26 is fitted with a spring or other biasing component, such as a formed flat spring 58 (as depicted in FIGS. 3, 4A, and 4B) or a torsion spring 60 (as depicted in FIGS. 5A and 5B). As will be appreciated by those of ordinary skill in the art, such biasing components may include elastic bodies or devices that may be distorted and that recover their original shape when released after being distorted. Similarly, a component or material that can store energy and release the energy to provide a gripping force, as described herein, may function as a spring or biasing component. For example, an overmolding material or composition, as discussed with regard to FIGS. 6-9, may have sufficient elasticity to function as a biasing component as discussed herein, with or without the additional gripping force provided by a component such as the flat spring 58 or the torsion spring 60. For the purpose of this example, however, the sensor 10 is provided with and discussed as including a flat spring 58 (in FIGS. 3 and 4A) or a torsion spring 60 (in FIG. 5A).

Referring to FIGS. 3 and 4A, a flat spring 58 is fitted at or near the end of the internal frame 26 that is opposite from where the finger, toe, or other patient appendage is inserted into the assembled sensor. In alternative embodiments, the flat spring 58 connects two different portions or halves of the internal frame 26 to form the internal frame 26. In the depicted embodiment, slots 64 are provided in the internal frame 26 that are engaged by complementary spring tabs 66 to fit the flat spring 58 to the internal frame 26. For example, in an embodiment in which the internal frame 26 is molded or formed as a relatively open, single-piece, as depicted in FIG. 2, the internal frame 26 may be bent from the relatively open configuration to a closed configuration, as depicted in FIGS. 3 and 4A. The flat spring 58 may be fitted or attached to the internal frame 26 when in the closed configuration to provide a biasing force that maintains the internal frame 26 in the closed configuration. Referring now to FIG. 5A, the torsion spring 60 may be similarly fitted or attached to the internal frame 26 when in the closed configuration to provide a biasing force that maintains the internal frame 26 in the closed configuration.

The flat spring 58 or torsion spring 60 may be constructed from a variety of materials or combinations of materials that provide the desired resiliency and clamping force. For example, in certain embodiments, the flat spring 58 or torsion spring 60 may be constructed from a metal alloy, such as stainless steel. In one such stainless steel flat spring embodiment, the flat spring 58 may be made from 301 high yield stainless steel that is 0.010 inch thick and that produces approximately 1.25 pounds of force at the optic plane (that is a plane through the emitter 22 and detector 24) with a finger pad separation of approximately 15 mm. In other embodiments, the flat spring 58 or torsion spring 60 may be constructed from materials such as plastics, polymers, composites, and so forth that provide the desired resilience and elasticity.

An overmolded sensor 10 (as discussed with regard to FIGS. 6-9) incorporating a flat spring 58, a torsion spring 60, or other biasing component, disposed on the internal frame 26 may be opened for placement on a patient's finger, toe, ear, or other appendage by applying a force to separate the top portion 46 and bottom portion 48 of the internal frame 26. For example, the flat spring 58 (in FIGS. 3 and 4A) or the torsion spring 60 (in FIG. 5A) provide or contribute to a closing force biasing the top portion 46 and the bottom portion 48 of the frame 26 together. An opposing force, however, may be applied to force the top portion 46 and bottom portion 48 apart. In the example depicted, an opposing force may be applied to projections, such as tabs 52, provided at the end of the internal frame 26 to which the flat spring 58 or torsion spring 60 is fitted such that the force provided by the respective spring is overcome. In this manner, the tabs 52 are moved toward one another while the top portion 46 and bottom portion 48 are moved apart from one another.

As noted above, in certain embodiments of the present technique, the frame 26 (such as a skeletal internal frame) is coated to form a unitary or integral sensor assembly, as depicted in FIGS. 6-9. Such overmolded embodiments may result in a sensor assembly in which the internal frame 26 is completely or substantially coated. In embodiments in which the internal frame 26 is formed or molded as a relatively open or flat structure, the overmolding or coating process may be performed prior to or subsequent to bending the internal frame 26 into the closed configuration.

For example, the sensor 10 may be formed by an injection molding process. In one example of such a process the internal frame 26 may be positioned within a die or mold of the desired shape for the sensor 10. A molten or otherwise unset overmold material may then be injected into the die or mold. For example, in one implementation, a molten thermoplastic elastomer at between about 400° F. to about 450° F. is injected into the mold. The overmold material may then be set, such as by cooling for one or more minutes or by chemical treatment, to form the sensor body about the internal frame 26. In certain embodiments, other sensor components, such as the emitter 22 and/or detector 24, may be attached or inserted into their respective housings or positions on the overmolded sensor body.

Alternatively, the optical components (such as emitter 22 and detector 24) and/or conductive structures (such as wires or flex circuits) may be placed on the internal frame 26 prior to overmolding. The internal frame 26 and associated components may then be positioned within a die or mold and overmolded, as previously described. To protect the emitter 22, detector 24, and or other electrical components, conventional techniques for protecting such components from excessive temperatures may be employed. For example, the emitter 22 and/or the detector 24 may include an associated clear window, such as a plastic or crystal window, in contact with the mold to prevent coating from being applied over the window. In one embodiment, the material in contact with such windows may be composed of a material, such as beryllium copper, which prevents the heat of the injection molding process from being conveyed through the window to the optical components. For example, in one embodiment, a beryllium copper material initially at about 40° F. is contacted with the windows associated with the emitter 22 and/or detector 24 to prevent coating of the windows and heat transfer to the respective optical components. As will be appreciated by those of ordinary skill in the art, the injection molding process described herein is merely one technique by which the frame 26 may be coated to form a sensor body, with or without associated sensing components. Other techniques which may be employed include, but are not limited to, dipping the frame 26 into a molten or otherwise unset coating material to coat the frame 26 or spraying the frame 26 with a molten or otherwise unset coating material to coat the frame 26. In such implementations, the coating material may be subsequently set, such as by cooling or chemical means, to form the coating. Such alternative techniques, to the extent that they may involve high temperatures, may include thermally protecting whatever optical components are present, such as by using beryllium copper or other suitable materials to prevent heat transfer through the windows associated with the optical components, as discussed above.

Figure 6:
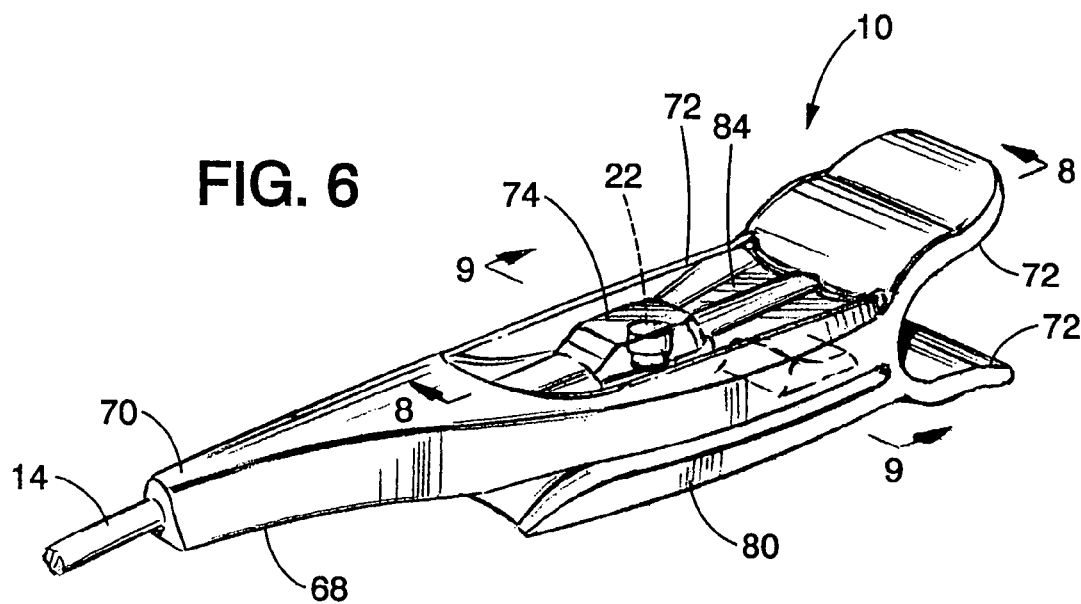
FIG. 6 illustrates a perspective view of an overmolded patient sensor, in accordance with aspects of the present technique.
Figure 7:
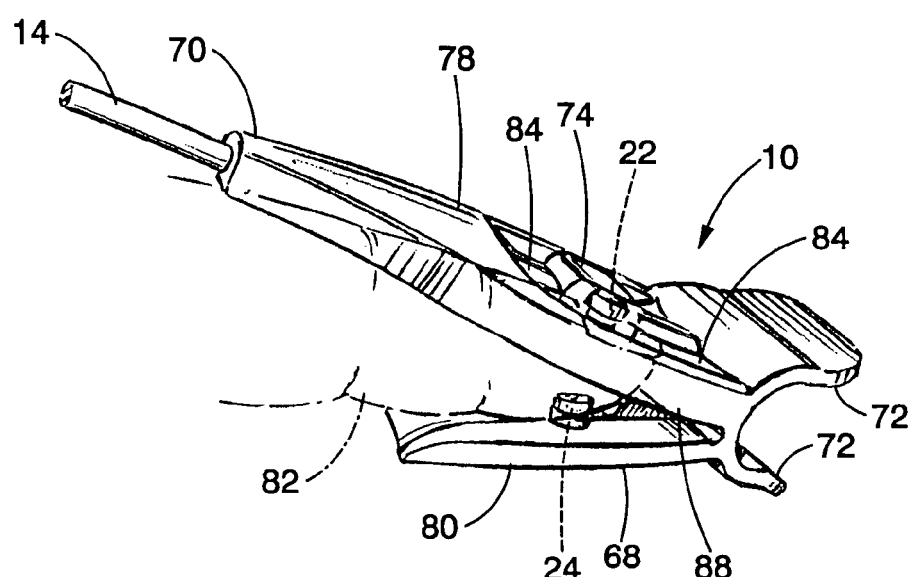
FIG. 7 illustrates the overmolded patient sensor of FIG. 6 in use on a patient's finger, in accordance with aspects of the present technique.

By such techniques, the frame 26, as well as the optical components and associated circuitry where desired, may be encased in a coating material 68 to form an integral or unitary assembly with no exposed or external moving parts of the internal frame 26. For example, as depicted in FIG. 6, the sensor 10 includes features of the underlying internal frame 26 that are now completely or partially overmolded, such as the overmolded external cable guide 70, tabs 72, emitter housing 74, and detector housing 76. In addition, the overmolded sensor 10 includes an overmolded upper portion 78 and lower portion 80 that may be fitted to the finger 82 of a patient (as depicted in FIG. 7), or to the toe, ear, or other appendage of the patient, as appropriate.

In one implementation, the overmolding or coating 68 is a thermoplastic elastomer or other conformable coating or material. In such embodiments, the thermoplastic elastomer may include compositions such as thermoplastic polyolefins, thermoplastic vulcanizate alloys, silicone, thermoplastic polyurethane, and so forth. In one embodiment, the overmolding material is polyurethane having a durometer of 15 Shore A. As will be appreciated by those of ordinary skill in the art, the overmolding composition may vary, depending on the varying degrees of conformability, durability, wettability, or other physical and/or chemical traits that are desired. Furthermore, the coating material 68 may be selected to provide additional spring force to that provided by the biasing component (such as flat spring 58 or torsion spring 60).

Furthermore, the coating material 68 may be selected based upon the desirability of a chemical bond between the internal frame 26 and the coating material 68. Such a chemical bond may be desirable for durability of the resulting overmolded sensor 10. For example, to prevent separation of the coating 68 from the internal frame 26, the material used to form the coating 68 may be selected such that the coating 68 bonds with some or all of the internal frame 26 during the overmolding process. In such embodiments, the coating 68 and the portions of the internal frame 26 to which the coating 68 is bonded are not separable, i.e., they form one continuous and generally inseparable structure.

Furthermore, in embodiments in which the coating 68 employed is liquid or fluid tight, such a sensor 10 may be easily maintained, cleaned, and/or disinfected by immersing the sensor into a disinfectant or cleaning solution or by rinsing the sensor 10 off, such as under running water. In particular, such an overmolded sensor assembly may be generally or substantially free of crevices, gaps, junctions or other surface irregularities typically associated with a multi-part construction which may normally allow the accumulation of biological detritus or residue. Such an absence of crevices and other irregularities may further facilitate the cleaning and care of the sensor 10.

Turning now to FIGS. 8 and 9, cross-sections of the coated sensor assembly 10 are depicted taken through transverse optical planes, represented by section line 8 and 9 of FIG. 6 respectively. FIGS. 8 and 9 depict, among other aspects of the sensor 10, the overmolding material 68 as well as underlying portions of the internal frame 26, such as the emitter housing 38 and detector housing 40, along with the respective emitter 22, detector 24, and signal transmission structures (such as wiring 83 or other structures for conducting electrical or optical signals). In the depicted embodiment, the emitter 22 and detector 24 are provided substantially flush with the patient facing surfaces of the sensor 10, as may be suitable for pulse oximetry applications. For other physiological monitoring applications, such as applications measuring tissue water fraction or other body fluid related metrics, other configurations may be desirable. For example, in such fluid measurement applications it may be desirable to provide one or both of the emitter 22 and detector 24 recessed relative to the patient facing surfaces of the sensor 10. Such modifications may be accomplished by proper configuration or design of a mold or die used in overmolding the internal frame 26 and/or by proper design of the emitter housing 38 or detector housing 40 of the internal frame 26.

In addition, as depicted in FIGS. 8 and 9, in certain embodiments portions 84 of the coating material 68 may be flexible, such as thin or membranous regions of coating material 68 disposed between structural supports 28 of a skeletal frame. Such flexible regions 84 allow a greater range of digit sizes to be accommodated for a given retention or clamping force of the sensor 10. For example, the flexible regions 84 may allow the emitter 22 and/or detector 24, to flex or expand apart from one another along the optical axis in embodiments in which the respective housings 38 and 40 are flexibly attached to the remainder of the frame 26. In this manner, the sensor 10 may accommodate differently sized digits. For instance, for a relatively small digit, the flexible region 84 may not be substantially deformed or vertically displaced, and therefore the emitter 22 and/or detector 24 are not substantially displaced either. For larger digits, however, the flexible regions 84 may be deformed or displaced to a greater extent to accommodate the digit, thereby displacing the emitter 22 and/or detector 24 as well. In addition, for medium to large digits, the flexible regions 84 may also increase retention of the sensor 10 on the digit by increasing the surface area to which the retaining force is applied.

Furthermore, as the flexible regions 84 deform, the force applied to the digit is spread out over a large area on the digit due to the deformation of the flexible region 84. In this way, a lower pressure on digits of all sizes may be provided for a given vertical force. Therefore, a suitable conforming fit may be obtained in which the emitter 22 and detector 24 are maintained in contact with the digit without the application of concentrated and/or undesirable amounts of force, thereby improving blood flow through the digit.

In the example depicted in FIGS. 6-9, flaps or side extensions 88 of the coating material 68 on the sides of the sensor 10 are depicted which facilitate the exclusion of environmental or ambient light from the interior of the sensor 10. Such extensions help prevent or reduce the detection of light from the outside environment, which may be inappropriately detected by the sensor 10 as correlating to the $SaO_2$. Thus, a pulse oximetry sensor may detect differences in signal modulations unrelated to the underlying $SaO_2$ level. In turn, this may impact the detected red-to-infrared modulation ratio and, consequently, the measured blood oxygen saturation ($SpO_2$) value. The conformability of the fit of sensor 10 and the use of side extensions 88, therefore, may help prevent or reduce such errors.

While the exemplary medical sensors 10 discussed herein are some examples of overmolded or coated medical devices, other such devices are also contemplated and fall within the scope of the present disclosure. For example, other medical sensors and/or contacts applied externally to a patient may be advantageously applied using an overmolded sensor body as discussed herein. Examples of such sensors or contacts may include glucose monitors or other sensors or contacts that are generally held adjacent to the skin of a patient such that a conformable and comfortable fit is desired. Similarly, and as noted above, devices for measuring tissue water fraction or other body fluid related metrics may utilize a sensor as described herein. Likewise, other spectrophotometric applications where a probe is attached to a patient may utilize a sensor as described herein.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims. Indeed, the present techniques may not only be applied to transmission type sensors for use in pulse oximetry, but also to retroflective and other sensor designs as well. Likewise, the present techniques are not limited to use on fingers and toes but may also be applied to placement on other body parts such as in embodiments configured for use on the ears or nose.

What is claimed is:

1. A sensor assembly, comprising:
   a frame comprising two or more structural supports;
   a coating provided over the frame, wherein the coating comprises at least one deformable region disposed between the two or more structural supports;
   at least one optical component disposed within the at least one deformable region, such that the at least one optical component is capable of moving relative to the two or more structural supports; and
   a biasing component attached to an end of the frame such that at least two different portions of the coated frame are biased closed in the absence of a sufficient opening force.

2. The sensor assembly of claim 1, wherein the at least one optical component comprises at least one of a light emitting diode or a photodetector.

3. The sensor assembly of claim 1, wherein the coating comprises a first deformable region disposed between first and second structural supports and a second deformable region disposed between third and fourth structural supports.

4. The sensor assembly of claim 3, wherein the at least one optical component comprises a light emitting diode disposed within the first deformable region and capable of moving relative to the first and second structural supports and a photodetector disposed within the second deformable region and capable of moving relative to the third and fourth structural supports.

5. The sensor assembly of claim 1, comprising one or more signal transmission structures connected to the at least optical component.

6. The sensor assembly of claim 1, wherein the sensor assembly comprises at least one of a pulse oximetry sensor, a sensor for measuring a water fraction, or a combination thereof.

7. The sensor assembly of claim 1, wherein the frame comprises a single molded part.

8. The sensor assembly of claim 1, wherein the frame comprises two or more parts joined to form the frame.

9. The sensor assembly of claim 1, wherein the coating comprises a thermoplastic elastomer.

10. The sensor assembly of claim 9, wherein the thermoplastic elastomer comprises at least one of a thermoplastic polyolefin, a thermoplastic vulcanizate alloy, thermoplastic polyurethane, silicone, or a combination thereof.

11. The sensor assembly of claim 1, wherein the coating comprises a conformable material.

12. The sensor assembly of claim 1, wherein no moving parts of the frame remain exposed from the coating.

13. The sensor assembly of claim 1, wherein the sensor assembly is fluid tight.

14. The sensor assembly of claim 1, wherein the coating is chemically bonded to the frame.

15. The sensor assembly of claim 1, comprising a pulse oximeter monitor configured to receive data from the at least one optical component.

16. The sensor assembly of claim 1, comprising a multi-parameter monitor configured to receive data from the at least one optical component.

17. The sensor assembly of claim 1, comprising at least one integrated circuit device.

18. The sensor assembly of claim 1, comprising a cable comprising one or more integrated circuits.

19. The sensor assembly of claim 1, comprising an adapter cable connected to one or more signal transmission structures of the sensor assembly.

20. The sensor assembly of claim 1, wherein the biasing component comprises at least one of a formed flat spring or a torsion spring.

21. The sensor assembly of claim 1, wherein the biasing component comprises a metal alloy.

22. The sensor assembly of claim 1, wherein the biasing component comprises a polymeric material.

* * * * *